United States Patent
Russel Burnham et al.

(10) Patent No.: US 6,326,170 B1
(45) Date of Patent: Dec. 4, 2001

(54) PROKARYOTIC POLYNUCLEOTIDES, POLYPEPTIDES AND THEIR USES

(75) Inventors: Martin Karl Russel Burnham, Barto; Michael Arthur Lonetto, Collegeville; Patrick Vernon Warren, Philadelphia, all of PA (US)

(73) Assignee: SmithKline Beecham Corp., Philadelphia, PA (US)

( * ) Notice: Subject to any disclaimer, the term of this patent is extended or adjusted under 35 U.S.C. 154(b) by 0 days.

(21) Appl. No.: 09/308,003

(22) PCT Filed: Sep. 14, 1998

(86) PCT No.: PCT/US98/18987

§ 371 Date: May 10, 1999

§ 102(e) Date: May 10, 1999

(87) PCT Pub. No.: WO99/12557

PCT Pub. Date: Mar. 18, 1999

Related U.S. Application Data

(60) Provisional application No. 60/058,710, filed on Sep. 12, 1997.

(51) Int. Cl.[7] ............... C12N 15/31; C12N 15/63; C12N 5/10; C07H 21/04
(52) U.S. Cl. ............... 435/69.3; 435/320.1; 435/325; 536/23.7
(58) Field of Search ............... 435/69.3, 320.1, 435/325; 536/23.7

(56) References Cited

FOREIGN PATENT DOCUMENTS

WO 97/03359   1/1997   (WO) .

OTHER PUBLICATIONS

Mondero, et al., Catabolite Repression in *Lactobacillus casei* ATCC 393 is Mediated by CcpA. J. Bacteriol, vol. 179, No. 21, pp. 6657–6664, esp. pp. 6659–6660, Nov. 1997.

Noel, et al., "Sequence of the URA1 gene encoding dihydroorotate dehydrogenase from the basidiomycete fungus *Agrocybe aegerita*", Gene, vol. 122, pp. 233–234, especially p. 234, (1992).

Hueck, et al., "Sequences of ccpA and two downstream *Bacillus megaterium* genes with homology to the motAB operon from *Bacillus subtilis*", Gene, vol. 143, pp. 147–148, especially p. 148, (1994).

Borchardt, et al., "Sequence analysis of the region downstream from a peptidoglycan hydrolase–encoding gene from *Staphylococcus aureus* NCTC8325", Gene, vol. 137, pp. 253–258, especially p. 255, (1993).

Fraser, et al., "Genomic sequence of a Lyme disease spirochaete, *Borrelia burgdorferi*", Nature, vol. 390, pp. 580–586, especially pp. 581 and 585–586, Dec. 11, 1997.

Kunst, et al., "The complete genome sequence of the Gram–positive bacterium *Bacillus subtilis*", Nature, vol. 390, pp. 249–256, especially pp. 255–256, Nov. 20, 1997.

Egeter, et al., "Catabolite repression mediated by the catabolite control protein Ccpa in *Staphylococcus xylosus*", Mol. Micorbiol., vol. 21, pp. 739–749, especially pp. 741 and 744–745, (1996).

Hueck, et al., "Analysis of a cis–active sequence mediating catabolite repression in Gram–positive bacteria", Res. Microbiol., vol. 145, pp. 503–518 (1994).

Fleischmann, et al, "Whole–Genome Random Sequencing and Assembly of *Haemophilus influenza* Rd", Science, vol. 269, pp. 496–512, especially pp. 498 and 508–511, Jul. 28, 1995.

*Primary Examiner*—Gary L. Kunz
*Assistant Examiner*—Stephen Gucker
(74) *Attorney, Agent, or Firm*—Edward R. Gimmi; Thomas S. Deibert; William T. Kana

(57) ABSTRACT

The invention provides novel polypeptides and polynucleotides encoding such polypeptides and methods for producing such polypeptides by recombinant techniques. Also provided are methods for utilizing such polypeptides to screen for antibacterial compounds.

12 Claims, No Drawings

SEQUENCE LISTING

<160> NUMBER OF SEQ ID NOS: 52

<210> SEQ ID NO 1
<211> LENGTH: 888
<212> TYPE: DNA
<213> ORGANISM: Staphylococcus aureus
<220> FEATURE:
<221> NAME/KEY: CDS
<222> LOCATION: (1)...(885)

<400> SEQUENCE: 1

```
atg gaa aca att att gaa gaa tat ttg cgt ttt ata caa att gaa aaa         48
Met Glu Thr Ile Ile Glu Glu Tyr Leu Arg Phe Ile Gln Ile Glu Lys
 1               5                  10                  15 gga cta agt tct aac aca att ggt gct tat aga cgt gat ttg aaa aag         96
Gly Leu Ser Ser Asn Thr Ile Gly Ala Tyr Arg Arg Asp Leu Lys Lys
             20                  25                  30 tat caa gat tat atg act gaa cat cat atc tcg cat att gat ttt ata        144
Tyr Gln Asp Tyr Met Thr Glu His His Ile Ser His Ile Asp Phe Ile
         35                  40                  45 gat cga caa tta att caa gag tgt ttg ggg cat tta ata gac caa ggg        192
Asp Arg Gln Leu Ile Gln Glu Cys Leu Gly His Leu Ile Asp Gln Gly
     50                  55                  60 caa tct gct aaa tct att gag cga ttt att tca aca atc cgt agt ttt        240
Gln Ser Ala Lys Ser Ile Glu Arg Phe Ile Ser Thr Ile Arg Ser Phe
 65                  70                  75                  80 cat caa ttt gct ata aga gaa aaa tat gcg gcg aaa gat cca acg gta        288
His Gln Phe Ala Ile Arg Glu Lys Tyr Ala Ala Lys Asp Pro Thr Val
                 85                  90                  95 tta tta gat tca cca aaa tat gac aaa aaa ttg cct gac gtt tta aat        336
Leu Leu Asp Ser Pro Lys Tyr Asp Lys Lys Leu Pro Asp Val Leu Asn
            100                 105                 110 gtt gac gaa gta ttg gct tta tta gaa acg cca gat tta aat aaa att        384
Val Asp Glu Val Leu Ala Leu Leu Glu Thr Pro Asp Leu Asn Lys Ile
```

```
aat gga tat cgt gat cgt acg atg tta gaa ctt ctg tac gca acg gga      432
Asn Gly Tyr Arg Asp Arg Thr Met Leu Glu Leu Leu Tyr Ala Thr Gly
        130                 135                 140 atg cgt gta tct gaa ttg ata cat tta gag tta gaa aac gtg aac tta      480
Met Arg Val Ser Glu Leu Ile His Leu Glu Leu Glu Asn Val Asn Leu
145                 150                 155                 160 ata atg gga ttt gta cgc gta ttt ggt aaa ggc gat aaa gaa aga att      528
Ile Met Gly Phe Val Arg Val Phe Gly Lys Gly Asp Lys Glu Arg Ile
                    165                 170                 175 gta cca tta ggc gac gca gtc att gag tac tta act act tat att gaa      576
Val Pro Leu Gly Asp Ala Val Ile Glu Tyr Leu Thr Thr Tyr Ile Glu
                180                 185                 190 acg att aga ccg caa ctt tta aaa aag act gtt act gaa gtc tta ttt      624
Thr Ile Arg Pro Gln Leu Leu Lys Lys Thr Val Thr Glu Val Leu Phe
            195                 200                 205 tta aat atg cat ggt aaa cct tta tca cga caa gca ata tgg aaa atg      672
Leu Asn Met His Gly Lys Pro Leu Ser Arg Gln Ala Ile Trp Lys Met
210                 215                 220 att aaa caa aat ggc gta aag gca aac att aaa aag aag tta acg cca      720
Ile Lys Gln Asn Gly Val Lys Ala Asn Ile Lys Lys Lys Leu Thr Pro
225                 230                 235                 240 cat acg tta cgc cac tct ttt gcg aca cat tta ttg gaa aat ggc gca      768
His Thr Leu Arg His Ser Phe Ala Thr His Leu Leu Glu Asn Gly Ala
                245                 250                 255 gat tta aga gca gtg caa gaa atg tta ggt cac tct gac ata tct act      816
Asp Leu Arg Ala Val Gln Glu Met Leu Gly His Ser Asp Ile Ser Thr
                260                 265                 270 acc caa ctc tat aca cat gtt tcg aaa tct caa att aaa aaa atg tat      864
Thr Gln Leu Tyr Thr His Val Ser Lys Ser Gln Ile Lys Lys Met Tyr
            275                 280                 285 tac cca ttt cat cct aaa aca taa                                      888
Tyr Pro Phe His Pro Lys Thr
        290                 295

<210> SEQ ID NO 2
<211> LENGTH: 1173
<212> TYPE: DNA
<213> ORGANISM: Staphylococcus aureus
<220> FEATURE:
<221> NAME/KEY: CDS
<222> LOCATION: (1)...(1170)

<400> SEQUENCE: 2 atg aca ctt tca aaa gag aca gaa gtg ata ttc gat tgg cgt aga ggt       48
Met Thr Leu Ser Lys Glu Thr Glu Val Ile Phe Asp Trp Arg Arg Gly
1               5                   10                  15 gtg gaa tat cat tca gct aac cca cca ctt tat gat ttt tca aca ttc       96
Val Glu Tyr His Ser Ala Asn Pro Pro Leu Tyr Asp Phe Ser Thr Phe
                20                  25                  30 cat caa aca agt ctt ggt ggc gat gtt aaa tat gat tat gca cga agt      144
His Gln Thr Ser Leu Gly Gly Asp Val Lys Tyr Asp Tyr Ala Arg Ser
            35                  40                  45 ggc aac cct aac cgt gaa ctt tta gaa gag aag tta gca cga tta gaa      192
Gly Asn Pro Asn Arg Glu Leu Leu Glu Glu Lys Leu Ala Arg Leu Glu
        50                  55                  60 cag gga aaa ttc gct ttt gct ttt gca tca ggt att gct gct att tca      240
Gln Gly Lys Phe Ala Phe Ala Phe Ala Ser Gly Ile Ala Ala Ile Ser
65                  70                  75                  80 gca gta ctt ttg act ttc aaa tct ggt gat cat gtc atc tta ccc gat      288
Ala Val Leu Leu Thr Phe Lys Ser Gly Asp His Val Ile Leu Pro Asp
```

```
                    85                      90                      95
gat gta tat ggc ggt act ttt cgc ctc act gag caa att ttg aat cga         336
Asp Val Tyr Gly Gly Thr Phe Arg Leu Thr Glu Gln Ile Leu Asn Arg
            100                     105                     110 ttt aat att gaa ttt aca acc gta gat act acc aag ctc gaa caa atc         384
Phe Asn Ile Glu Phe Thr Thr Val Asp Thr Thr Lys Leu Glu Gln Ile
            115                     120                     125 gag ggt gcc att caa tca aac aca aaa tta att tat atc gaa aca cca         432
Glu Gly Ala Ile Gln Ser Asn Thr Lys Leu Ile Tyr Ile Glu Thr Pro
130                     135                     140 tcg aat ccc tgt ttt aaa att act gat atc aaa gct gtt tct aaa ata         480
Ser Asn Pro Cys Phe Lys Ile Thr Asp Ile Lys Ala Val Ser Lys Ile
145                     150                     155                     160 gcc gaa aag cat gaa cta ctg gta gct gtg gac aat aca ttt atg aca         528
Ala Glu Lys His Glu Leu Leu Val Ala Val Asp Asn Thr Phe Met Thr
                165                     170                     175 ccg tta ggc caa tca cct tta tta ctt ggc gct gat att gtc att cat         576
Pro Leu Gly Gln Ser Pro Leu Leu Leu Gly Ala Asp Ile Val Ile His
            180                     185                     190 agt gct acc aaa ttt tta agt gga cat agc gat tta att gct ggt gct         624
Ser Ala Thr Lys Phe Leu Ser Gly His Ser Asp Leu Ile Ala Gly Ala
            195                     200                     205 gtc att act aat att gag cca att agt gaa gct ctt tat tta aac cac         672
Val Ile Thr Asn Ile Glu Pro Ile Ser Glu Ala Leu Tyr Leu Asn His
210                     215                     220 aat ggt aca ggc aat atg tta tct gct caa gat agc tgg aca ctt gct         720
Asn Gly Thr Gly Asn Met Leu Ser Ala Gln Asp Ser Trp Thr Leu Ala
225                     230                     235                     240 aaa cat tta aag aca ttt cca atc aga ttt aaa caa tct gtc gaa aac         768
Lys His Leu Lys Thr Phe Pro Ile Arg Phe Lys Gln Ser Val Glu Asn
                245                     250                     255 gcg caa aaa atc gtg tca ttt tta ata aag caa gat gaa att tca gaa         816
Ala Gln Lys Ile Val Ser Phe Leu Ile Lys Gln Asp Glu Ile Ser Glu
            260                     265                     270 gtt tat tat ccg gga ctc act act gct cat tta gaa caa gct aaa aat         864
Val Tyr Tyr Pro Gly Leu Thr Thr Ala His Leu Glu Gln Ala Lys Asn
            275                     280                     285 ggc ggt gcc gtt att ggc ttt cgt tta gct gat gag tct aaa gca caa         912
Gly Gly Ala Val Ile Gly Phe Arg Leu Ala Asp Glu Ser Lys Ala Gln
        290                     295                     300 caa ttt gtc gat gca ctg aca tta cca ctc gtt tca gtg agt ctg ggt         960
Gln Phe Val Asp Ala Leu Thr Leu Pro Leu Val Ser Val Ser Leu Gly
305                     310                     315                     320 ggt gtt gaa acg atc ctt tca cat cca gca aca atg tct cac gct gca        1008
Gly Val Glu Thr Ile Leu Ser His Pro Ala Thr Met Ser His Ala Ala
                325                     330                     335 cta cct gaa gaa gtg aga caa gaa cgt ggt atc act ttc ggt cta ttc        1056
Leu Pro Glu Glu Val Arg Gln Glu Arg Gly Ile Thr Phe Gly Leu Phe
            340                     345                     350 cga tta agt gtt ggt ctc gaa gat cct gat gaa ctc att gca gac atc        1104
Arg Leu Ser Val Gly Leu Glu Asp Pro Asp Glu Leu Ile Ala Asp Ile
            355                     360                     365 aaa tac gca tta aag gag gca tcc aat gag tca att ccc tca cac aat        1152
Lys Tyr Ala Leu Lys Glu Ala Ser Asn Glu Ser Ile Pro Ser His Asn
370                     375                     380 tgt aag ata atg ttt aag tag                                            1173
Cys Lys Ile Met Phe Lys
385                     390
```

```
<210> SEQ ID NO 3
<211> LENGTH: 1365
<212> TYPE: DNA
<213> ORGANISM: Staphylococcus aureus
<220> FEATURE:
<221> NAME/KEY: CDS
<222> LOCATION: (1)...(1365)
<221> NAME/KEY: misc_feature
<222> LOCATION: (1)...(1365)
<223> OTHER INFORMATION: n = A,T,C or G

<400> SEQUENCE: 3
```

| | | | | | | | | | | | | | | | | |
|---|---|---|---|---|---|---|---|---|---|---|---|---|---|---|---|---|
| agc | cca | agc | ctc | ttt | cac | aaa | agt | caa | acc | atg | aca | acg | cca | atg | tta | 48 |
| Ser | Pro | Ser | Leu | Phe | His | Lys | Ser | Gln | Thr | Met | Thr | Thr | Pro | Met | Leu | |
| 1 | | | | 5 | | | | | 10 | | | | | 15 | | |
| agt | tta | ggg | aat | gca | ttt | aat | gag | gat | gat | ttg | aga | aaa | ttc | gac | caa | 96 |
| Ser | Leu | Gly | Asn | Ala | Phe | Asn | Glu | Asp | Asp | Leu | Arg | Lys | Phe | Asp | Gln | |
| | | | 20 | | | | | 25 | | | | | 30 | | | |
| cgc | ata | cgt | gaa | caa | att | ggc | aac | gtt | gaa | tat | atg | tgc | gaa | tta | aaa | 144 |
| Arg | Ile | Arg | Glu | Gln | Ile | Gly | Asn | Val | Glu | Tyr | Met | Cys | Glu | Leu | Lys | |
| | | 35 | | | | | 40 | | | | | 45 | | | | |
| att | gat | ggc | tta | gca | gta | tca | ttg | aaa | tat | gtt | gat | gga | tac | ttc | gtt | 192 |
| Ile | Asp | Gly | Leu | Ala | Val | Ser | Leu | Lys | Tyr | Val | Asp | Gly | Tyr | Phe | Val | |
| 50 | | | | | 55 | | | | | 60 | | | | | | |
| caa | ggt | tta | aca | cgt | ggt | gat | gga | aca | aca | ggt | gaa | gat | att | acc | gaa | 240 |
| Gln | Gly | Leu | Thr | Arg | Gly | Asp | Gly | Thr | Thr | Gly | Glu | Asp | Ile | Thr | Glu | |
| 65 | | | | | 70 | | | | | 75 | | | | | 80 | |
| aat | tta | aaa | aca | att | cat | gcg | ata | cct | ttg | aaa | atg | aaa | gaa | cca | tta | 288 |
| Asn | Leu | Lys | Thr | Ile | His | Ala | Ile | Pro | Leu | Lys | Met | Lys | Glu | Pro | Leu | |
| | | | | 85 | | | | | 90 | | | | | 95 | | |
| aat | gta | gaa | gtt | cgt | ggt | gaa | gca | tat | atg | ccg | aga | cgt | tca | ttt | tta | 336 |
| Asn | Val | Glu | Val | Arg | Gly | Glu | Ala | Tyr | Met | Pro | Arg | Arg | Ser | Phe | Leu | |
| | | | 100 | | | | | 105 | | | | | 110 | | | |
| cga | tta | aat | gaa | gaa | aaa | gaa | aaa | aat | gat | gag | cag | tta | ttt | gca | aat | 384 |
| Arg | Leu | Asn | Glu | Glu | Lys | Glu | Lys | Asn | Asp | Glu | Gln | Leu | Phe | Ala | Asn | |
| | | 115 | | | | | 120 | | | | | 125 | | | | |
| cca | aga | aac | gct | gct | gcg | gga | tca | tta | aga | cag | tta | gat | tct | aaa | tta | 432 |
| Pro | Arg | Asn | Ala | Ala | Ala | Gly | Ser | Leu | Arg | Gln | Leu | Asp | Ser | Lys | Leu | |
| 130 | | | | | 135 | | | | | 140 | | | | | | |
| acg | gca | aaa | cga | aag | cta | agc | gta | ttt | ata | tat | agt | gtc | aat | gat | ttc | 480 |
| Thr | Ala | Lys | Arg | Lys | Leu | Ser | Val | Phe | Ile | Tyr | Ser | Val | Asn | Asp | Phe | |
| 145 | | | | | 150 | | | | | 155 | | | | | 160 | |
| act | gat | ttc | aat | gcg | cgt | tcg | caa | agt | gaa | gca | tta | gat | gag | tta | gat | 528 |
| Thr | Asp | Phe | Asn | Ala | Arg | Ser | Gln | Ser | Glu | Ala | Leu | Asp | Glu | Leu | Asp | |
| | | | | 165 | | | | | 170 | | | | | 175 | | |
| aaa | tta | ggt | ttt | aca | acg | aat | aaa | aat | aga | gcg | cgt | gta | aat | aat | atc | 576 |
| Lys | Leu | Gly | Phe | Thr | Thr | Asn | Lys | Asn | Arg | Ala | Arg | Val | Asn | Asn | Ile | |
| | | | 180 | | | | | 185 | | | | | 190 | | | |
| gat | ggt | gtt | tta | gag | tat | att | gaa | aaa | tgg | aca | agc | caa | aga | gag | tca | 624 |
| Asp | Gly | Val | Leu | Glu | Tyr | Ile | Glu | Lys | Trp | Thr | Ser | Gln | Arg | Glu | Ser | |
| | | 195 | | | | | 200 | | | | | 205 | | | | |
| tta | cct | tat | gat | att | gat | ggg | att | gtt | att | aag | gtt | aat | gat | tta | gat | 672 |
| Leu | Pro | Tyr | Asp | Ile | Asp | Gly | Ile | Val | Ile | Lys | Val | Asn | Asp | Leu | Asp | |
| 210 | | | | | 215 | | | | | 220 | | | | | | |
| caa | cag | gat | gag | atg | gga | ttc | aca | caa | aaa | tct | cct | aga | tgg | gcc | att | 720 |
| Gln | Gln | Asp | Glu | Met | Gly | Phe | Thr | Gln | Lys | Ser | Pro | Arg | Trp | Ala | Ile | |
| 225 | | | | | 230 | | | | | 235 | | | | | 240 | |
| gct | tat | aaa | ttt | cca | gct | gag | gaa | gta | gta | act | aaa | tta | tta | gat | att | 768 |
| Ala | Tyr | Lys | Phe | Pro | Ala | Glu | Glu | Val | Val | Thr | Lys | Leu | Leu | Asp | Ile | |
| | | | | 245 | | | | | 250 | | | | | 255 | | |
| gaa | tta | agt | att | gga | cga | aca | ggt | gta | gtc | aca | cct | act | gct | att | tta | 816 |
| Glu | Leu | Ser | Ile | Gly | Arg | Thr | Gly | Val | Val | Thr | Pro | Thr | Ala | Ile | Leu | |

| | | | | | | | | | | | | | | | | |
|---|---|---|---|---|---|---|---|---|---|---|---|---|---|---|---|---|
| | | | | 260 | | | | | 265 | | | | | 270 | | |
| gaa | cca | gta | aaa | gta | gct | ggt | aca | act | gta | tca | aga | gca | tct | ttg | cac | 864 |
| Glu | Pro | Val | Lys | Val | Ala | Gly | Thr | Thr | Val | Ser | Arg | Ala | Ser | Leu | His | |
| | | 275 | | | | 280 | | | | | 285 | | | | | |
| aat | gag | gat | tta | att | cat | gac | aga | gat | att | cga | att | ggt | gat | agt | gtt | 912 |
| Asn | Glu | Asp | Leu | Ile | His | Asp | Arg | Asp | Ile | Arg | Ile | Gly | Asp | Ser | Val | |
| | 290 | | | | | 295 | | | | | 300 | | | | | |
| gta | gtg | aaa | aaa | gca | ggt | gac | atc | ata | cct | gaa | gtt | gta | cgt | agt | att | 960 |
| Val | Val | Lys | Lys | Ala | Gly | Asp | Ile | Ile | Pro | Glu | Val | Val | Arg | Ser | Ile | |
| 305 | | | | | 310 | | | | | 315 | | | | | 320 | |
| cca | gaa | cgt | aga | cct | gag | gat | gct | gtc | aca | tat | cat | atg | cca | acc | cat | 1008 |
| Pro | Glu | Arg | Arg | Pro | Glu | Asp | Ala | Val | Thr | Tyr | His | Met | Pro | Thr | His | |
| | | | 325 | | | | | 330 | | | | | 335 | | | |
| tgt | cca | agt | tgt | gga | cat | gaa | tta | gta | cgt | att | gaa | ggc | gaa | gta | gca | 1056 |
| Cys | Pro | Ser | Cys | Gly | His | Glu | Leu | Val | Arg | Ile | Glu | Gly | Glu | Val | Ala | |
| | | | 340 | | | | | 345 | | | | | 350 | | | |
| ctt | cgt | tgc | att | aat | cca | aaa | tgc | caa | gca | caa | ctt | gtt | gaa | gga | tta | 1104 |
| Leu | Arg | Cys | Ile | Asn | Pro | Lys | Cys | Gln | Ala | Gln | Leu | Val | Glu | Gly | Leu | |
| | | 355 | | | | | 360 | | | | | 365 | | | | |
| att | cac | ttt | gta | tca | aga | caa | gcc | atg | aat | att | gat | ggt | tta | ggc | act | 1152 |
| Ile | His | Phe | Val | Ser | Arg | Gln | Ala | Met | Asn | Ile | Asp | Gly | Leu | Gly | Thr | |
| | 370 | | | | | 375 | | | | | 380 | | | | | |
| aaa | att | att | caa | cag | ctt | tat | caa | agc | gaa | tta | att | aaa | gat | gtt | gct | 1200 |
| Lys | Ile | Ile | Gln | Gln | Leu | Tyr | Gln | Ser | Glu | Leu | Ile | Lys | Asp | Val | Ala | |
| 385 | | | | | 390 | | | | | 395 | | | | | 400 | |
| gat | atc | tcc | tat | tta | aca | gaa | gaa | gat | tta | tta | cct | tta | gat | aga | atg | 1248 |
| Asp | Ile | Ser | Tyr | Leu | Thr | Glu | Glu | Asp | Leu | Leu | Pro | Leu | Asp | Arg | Met | |
| | | | | 405 | | | | | 410 | | | | | 415 | | |
| gcg | cag | aaa | aaa | gtt | gat | aac | tta | tta | gct | gcc | att | caa | caa | gct | aag | 1296 |
| Ala | Gln | Lys | Lys | Val | Asp | Asn | Leu | Leu | Ala | Ala | Ile | Gln | Gln | Ala | Lys | |
| | | | 420 | | | | | 425 | | | | | 430 | | | |
| gac | aac | tct | nta | gaa | aat | tta | tta | ttt | ggt | cta | ggt | atc | agg | cat | cta | 1344 |
| Asp | Asn | Ser | Xaa | Glu | Asn | Leu | Leu | Phe | Gly | Leu | Gly | Ile | Arg | His | Leu | |
| | | 435 | | | | | 440 | | | | | 445 | | | | |
| ggt | gtt | aaa | gcg | agc | aag | tgt | | | | | | | | | | 1365 |
| Gly | Val | Lys | Ala | Ser | Lys | Cys | | | | | | | | | | |
| | 450 | | | | 455 | | | | | | | | | | | |

<210> SEQ ID NO 4
<211> LENGTH: 990
<212> TYPE: DNA
<213> ORGANISM: Staphylococcus aureus
<220> FEATURE:
<221> NAME/KEY: CDS
<222> LOCATION: (1)...(987)

<400> SEQUENCE: 4

| | | | | | | | | | | | | | | | | |
|---|---|---|---|---|---|---|---|---|---|---|---|---|---|---|---|---|
| atg | aca | gtt | act | ata | tat | gat | gta | gca | aga | gaa | gcg | cgt | gtc | tct | atg | 48 |
| Met | Thr | Val | Thr | Ile | Tyr | Asp | Val | Ala | Arg | Glu | Ala | Arg | Val | Ser | Met | |
| 1 | | | | 5 | | | | | 10 | | | | | 15 | | |
| gcc | aca | gtg | tcg | cgt | gtt | gtt | aat | ggg | aac | caa | aat | gtt | aaa | gca | gaa | 96 |
| Ala | Thr | Val | Ser | Arg | Val | Val | Asn | Gly | Asn | Gln | Asn | Val | Lys | Ala | Glu | |
| | | | 20 | | | | | 25 | | | | | 30 | | | |
| act | aaa | aat | aaa | gtt | aac | gaa | gtc | att | aag | cgt | ttg | aat | tat | cgt | cca | 144 |
| Thr | Lys | Asn | Lys | Val | Asn | Glu | Val | Ile | Lys | Arg | Leu | Asn | Tyr | Arg | Pro | |
| | | 35 | | | | | 40 | | | | | 45 | | | | |
| aat | gct | gtt | gct | aga | ggt | tta | gct | agt | aaa | aag | aca | aca | aca | gta | ggt | 192 |
| Asn | Ala | Val | Ala | Arg | Gly | Leu | Ala | Ser | Lys | Lys | Thr | Thr | Thr | Val | Gly | |
| | 50 | | | | | 55 | | | | | 60 | | | | | |
| gtg | atc | att | cca | gat | ata | tct | aat | atc | tat | tat | tca | caa | ctt | gct | cgt | 240 |
| Val | Ile | Ile | Pro | Asp | Ile | Ser | Asn | Ile | Tyr | Tyr | Ser | Gln | Leu | Ala | Arg | |

```
              65                  70                  75                  80
gga ctt gaa gat att gca aca atg tat aaa tat cac tca att att tca           288
Gly Leu Glu Asp Ile Ala Thr Met Tyr Lys Tyr His Ser Ile Ile Ser
                    85                  90                  95 aat tca gat aac gat cct gaa aag gaa aaa gaa att ttt aat aac tta           336
Asn Ser Asp Asn Asp Pro Glu Lys Glu Lys Glu Ile Phe Asn Asn Leu
                100                 105                 110 tta agt aaa caa gtt gat ggt att att ttc ctt ggt gga aca att act           384
Leu Ser Lys Gln Val Asp Gly Ile Ile Phe Leu Gly Gly Thr Ile Thr
            115                 120                 125 gaa gaa atg aaa gaa ttg ata aat caa tca tct gta cct gta gta gta           432
Glu Glu Met Lys Glu Leu Ile Asn Gln Ser Ser Val Pro Val Val Val
        130                 135                 140 tca gga aca aat ggt aag gat gca cat ata gca tca gtt aat att gat           480
Ser Gly Thr Asn Gly Lys Asp Ala His Ile Ala Ser Val Asn Ile Asp
145                 150                 155                 160 ttt act gaa gct gcg aaa gaa att acg gga gaa tta att gaa aaa ggc           528
Phe Thr Glu Ala Ala Lys Glu Ile Thr Gly Glu Leu Ile Glu Lys Gly
                165                 170                 175 gct aaa tca ttt gct tta gta ggt gga gaa cat tct aaa aaa gct caa           576
Ala Lys Ser Phe Ala Leu Val Gly Gly Glu His Ser Lys Lys Ala Gln
            180                 185                 190 gaa gat gtt tta gaa ggt tta act gaa gtg tta aat aaa aat ggc ctt           624
Glu Asp Val Leu Glu Gly Leu Thr Glu Val Leu Asn Lys Asn Gly Leu
        195                 200                 205 caa tta ggt gat aca ttg aat tgt tct ggt gct gaa agt tat aaa gaa           672
Gln Leu Gly Asp Thr Leu Asn Cys Ser Gly Ala Glu Ser Tyr Lys Glu
    210                 215                 220 ggc gta aaa gct ttt gct aaa atg aaa ggc aat ttg cca gat gcc att           720
Gly Val Lys Ala Phe Ala Lys Met Lys Gly Asn Leu Pro Asp Ala Ile
225                 230                 235                 240 tta tgt atc agc gac gaa gaa gca att ggt att atg cat agt gca atg           768
Leu Cys Ile Ser Asp Glu Glu Ala Ile Gly Ile Met His Ser Ala Met
                245                 250                 255 gat gct ggt att aaa gtt cca gag gaa tta caa att att agt ttc aat           816
Asp Ala Gly Ile Lys Val Pro Glu Glu Leu Gln Ile Ile Ser Phe Asn
            260                 265                 270 aat aca cga tta gtt gag atg gtt aga cca caa ctt tct agt gtt att           864
Asn Thr Arg Leu Val Glu Met Val Arg Pro Gln Leu Ser Ser Val Ile
        275                 280                 285 caa cca tta tat gat atc ggt gca gta ggg atg cgc tta tta aca aaa           912
Gln Pro Leu Tyr Asp Ile Gly Ala Val Gly Met Arg Leu Leu Thr Lys
    290                 295                 300 tat atg aac gat gaa aag ata caa gaa cca aat gta gtt tta cct cac           960
Tyr Met Asn Asp Glu Lys Ile Gln Glu Pro Asn Val Val Leu Pro His
305                 310                 315                 320 aga att gaa tac cga gga act aca aaa taa                                   990
Arg Ile Glu Tyr Arg Gly Thr Thr Lys
                325

<210> SEQ ID NO 5
<211> LENGTH: 207
<212> TYPE: DNA
<213> ORGANISM: Staphylococcus aureus
<220> FEATURE:
<221> NAME/KEY: CDS
<222> LOCATION: (1)...(207)

<400> SEQUENCE: 5 ata aaa aga atg gac gta gat aat atg agt gat tat aaa tta aaa ata           48
Ile Lys Arg Met Asp Val Asp Asn Met Ser Asp Tyr Lys Leu Lys Ile
```

-continued

```
            1               5               10              15
att gaa ttg atc aaa agt gat ata aca ggt tac caa att cac aaa caa    96
Ile Glu Leu Ile Lys Ser Asp Ile Thr Gly Tyr Gln Ile His Lys Gln
                20              25              30 act ggc gta gcg caa tat gta att tca caa tta agg caa gga aag cgc    144
Thr Gly Val Ala Gln Tyr Val Ile Ser Gln Leu Arg Gln Gly Lys Arg
        35              40              45 gaa gta gat aac tta act tta aat aca act gaa aaa cta tac agt tac    192
Glu Val Asp Asn Leu Thr Leu Asn Thr Thr Glu Lys Leu Tyr Ser Tyr
    50              55              60 gca cga caa gtg tta                                                207
Ala Arg Gln Val Leu
 65

<210> SEQ ID NO 6
<211> LENGTH: 1167
<212> TYPE: DNA
<213> ORGANISM: Staphylococcus aureus
<220> FEATURE:
<221> NAME/KEY: CDS
<222> LOCATION: (1)...(1164)

<400> SEQUENCE: 6 atg att aat gaa aga gaa gtg ttt att ttg ata tat cta gat aat gcg    48
Met Ile Asn Glu Arg Glu Val Phe Ile Leu Ile Tyr Leu Asp Asn Ala
 1               5              10              15 gca acg acg aaa gca ttt gat gaa gtg ttg gat act tat gtg aaa gta    96
Ala Thr Thr Lys Ala Phe Asp Glu Val Leu Asp Thr Tyr Val Lys Val
                20              25              30 aat caa tca atg tat gtt aat cct aat agt ccg cat aaa gct ggt tcg    144
Asn Gln Ser Met Tyr Val Asn Pro Asn Ser Pro His Lys Ala Gly Ser
        35              40              45 cag gca aat caa tta cta caa caa gca aaa gcc caa att aat gca atg    192
Gln Ala Asn Gln Leu Leu Gln Gln Ala Lys Ala Gln Ile Asn Ala Met
    50              55              60 att aat tca aaa aca aat tat gat gtt gta ttc act agt ggt gca act    240
Ile Asn Ser Lys Thr Asn Tyr Asp Val Val Phe Thr Ser Gly Ala Thr
 65              70              75              80 gaa tcc aat aat ctt gct tta aaa ggt att gcc tat cgt aaa ttt gat    288
Glu Ser Asn Asn Leu Ala Leu Lys Gly Ile Ala Tyr Arg Lys Phe Asp
                85              90              95 aca gcg aag gaa ata att aca tcc gtg tta gag cat ccg tcc gta tta    336
Thr Ala Lys Glu Ile Ile Thr Ser Val Leu Glu His Pro Ser Val Leu
                100             105             110 gag gtt gta aga tat ttg gaa gca cac gaa gga ttt aaa gtt aaa tat    384
Glu Val Val Arg Tyr Leu Glu Ala His Glu Gly Phe Lys Val Lys Tyr
        115             120             125 gtt gat gta aag aaa gat ggc agt att aac tta gaa cac ttc aaa gaa    432
Val Asp Val Lys Lys Asp Gly Ser Ile Asn Leu Glu His Phe Lys Glu
    130             135             140 tta gtg tca gac aaa gtc ggt tta gta aca tgt atg tat gta aat aat    480
Leu Val Ser Asp Lys Val Gly Leu Val Thr Cys Met Tyr Val Asn Asn
145             150             155             160 gta act gga caa ata cag cct att cca caa atg gct aaa gtt ata aaa    528
Val Thr Gly Gln Ile Gln Pro Ile Pro Gln Met Ala Lys Val Ile Lys
                165             170             175 aat tat cct aag gca cat ttt cat gta gat gcg gct caa gca ttc ggc    576
Asn Tyr Pro Lys Ala His Phe His Val Asp Ala Ala Gln Ala Phe Gly
        180             185             190 aaa att tca atg gat ctc aat aac ata gat agt att agt tta agt gga    624
Lys Ile Ser Met Asp Leu Asn Asn Ile Asp Ser Ile Ser Leu Ser Gly
```

```
                195                 200                     205
cac aag ttt aat ggt tta aaa gga caa ggc gtc tta ctt gta aat cac       672
His Lys Phe Asn Gly Leu Lys Gly Gln Gly Val Leu Leu Val Asn His
        210                 215                     220 ata caa aat gtt gga cca tct gtc cat ggt ggt ggt caa gaa tat ggc       720
Ile Gln Asn Val Gly Pro Ser Val His Gly Gly Gly Gln Glu Tyr Gly
225                 230                 235                     240 gtt aga agt gga aca gtt aat ttg cca aat gat att gca atg gtt aaa       768
Val Arg Ser Gly Thr Val Asn Leu Pro Asn Asp Ile Ala Met Val Lys
                245                 250                     255 gcg atg aag ata gct aat gaa aac ttt gaa gca ttg aat gca ttt gtt       816
Ala Met Lys Ile Ala Asn Glu Asn Phe Glu Ala Leu Asn Ala Phe Val
            260                 265                     270 act gag tta aat aat gac gtc cgt caa ttt tta aat aaa tat cat gga       864
Thr Glu Leu Asn Asn Asp Val Arg Gln Phe Leu Asn Lys Tyr His Gly
        275                 280                     285 gtt tat att aat tct tca act tca ggt tca cca ttc gtt tta aat att       912
Val Tyr Ile Asn Ser Ser Thr Ser Gly Ser Pro Phe Val Leu Asn Ile
290                 295                 300 agt ttt cct ggc gta aaa ggt gaa gta tta gtt aat gct ttt tca aaa       960
Ser Phe Pro Gly Val Lys Gly Glu Val Leu Val Asn Ala Phe Ser Lys
305                 310                 315                     320 tat gac att atg ata tct acg acg agt gct tgt tca tct aaa cgt aat      1008
Tyr Asp Ile Met Ile Ser Thr Thr Ser Ala Cys Ser Ser Lys Arg Asn
                325                 330                     335 aaa tta aat gaa gta ttg gct gca atg gga tta tca gac aaa tct att      1056
Lys Leu Asn Glu Val Leu Ala Ala Met Gly Leu Ser Asp Lys Ser Ile
            340                 345                     350 gaa ggt agt ata aga tta tca ttt ggg gct act aca act aaa gaa gat      1104
Glu Gly Ser Ile Arg Leu Ser Phe Gly Ala Thr Thr Thr Lys Glu Asp
        355                 360                     365 ata gca agg ttt aaa gaa ata ttt atc atc att tat gag gaa att aag      1152
Ile Ala Arg Phe Lys Glu Ile Phe Ile Ile Ile Tyr Glu Glu Ile Lys
        370                 375                     380 gag ttg cta aaa taa                                                  1167
Glu Leu Leu Lys
385

<210> SEQ ID NO 7
<211> LENGTH: 537
<212> TYPE: DNA
<213> ORGANISM: Staphylococcus aureus
<220> FEATURE:
<221> NAME/KEY: CDS
<222> LOCATION: (1)...(537)

<400> SEQUENCE: 7 ctg cta ctt ttt gga aac gac gct cta atg ccg aat ctt ttt caa tat        48
Leu Leu Leu Phe Gly Asn Asp Ala Leu Met Pro Asn Leu Phe Gln Tyr
1               5                   10                      15 att ctc gat att cat tta gag ctg ttg cac ccc ata caa tgt aac tct        96
Ile Leu Asp Ile His Leu Glu Leu Leu His Pro Ile Gln Cys Asn Ser
            20                  25                      30 cgt cgt gct aac att ggt ttt agc atg ttg cct gca tcc atg gca cca       144
Arg Arg Ala Asn Ile Gly Phe Ser Met Leu Pro Ala Ser Met Ala Pro
        35                  40                      45 tct gtt tta cca gca cct aca agc ata tgg att tca tca ata aat aat       192
Ser Val Leu Pro Ala Pro Thr Ser Ile Trp Ile Ser Ser Ile Asn Asn
    50                  55                      60 ata att cta cca tca gac tct tta act tct ttt agg act gct ttt aat       240
Ile Ile Leu Pro Ser Asp Ser Leu Thr Ser Phe Arg Thr Ala Phe Asn
```

```
ctc tct tca aat tca cca cga tat tta gcg ccc gct act aat gcg ctt      288
Leu Ser Ser Asn Ser Pro Arg Tyr Leu Ala Pro Ala Thr Asn Ala Leu
             85                  90                  95 aaa tct aac tca aaa aca gtt tta tct aat aat gat tct ggc aca tct      336
Lys Ser Asn Ser Lys Thr Val Leu Ser Asn Asn Asp Ser Gly Thr Ser
            100                 105                 110 ttc tta act ata cgt tgc gct aat cct tca aca att gca gtt tta cca      384
Phe Leu Thr Ile Arg Cys Ala Asn Pro Ser Thr Ile Ala Val Leu Pro
            115                 120                 125 aca cct ggt tca cca atg agc aca ggg ttg ttt tta gtt tta cga ctt      432
Thr Pro Gly Ser Pro Met Ser Thr Gly Leu Phe Leu Val Leu Arg Leu
        130                 135                 140 aaa ata cga atc gta ttt cga att tct tca tct ctt cct ata aca gga      480
Lys Ile Arg Ile Val Phe Arg Ile Ser Ser Ser Leu Pro Ile Thr Gly
145                 150                 155                 160 tcc att tta cct tgt cta act tct tct act aag tcg cgg cca tat tta      528
Ser Ile Leu Pro Cys Leu Thr Ser Ser Thr Lys Ser Arg Pro Tyr Leu
                165                 170                 175 gct cgt gcc                                                          537
Ala Arg Ala <210> SEQ ID NO 8
<211> LENGTH: 1182
<212> TYPE: DNA
<213> ORGANISM: Staphylococcus aureus
<220> FEATURE:
<221> NAME/KEY: CDS
<222> LOCATION: (1)...(1179)

<400> SEQUENCE: 8 gtg tca gaa tta att ata tat aac ggc aaa gtt tat act gaa gat ggc       48
Val Ser Glu Leu Ile Ile Tyr Asn Gly Lys Val Tyr Thr Glu Asp Gly
  1               5                  10                  15 aaa atc gat aat ggt tac att cat gtg aaa gat gga cag att gtt gca       96
Lys Ile Asp Asn Gly Tyr Ile His Val Lys Asp Gly Gln Ile Val Ala
             20                  25                  30 att gga gaa gta aat gat aaa gca gcg att gat aat gat acg aca aat      144
Ile Gly Glu Val Asn Asp Lys Ala Ala Ile Asp Asn Asp Thr Thr Asn
         35                  40                  45 aaa att caa gtg att gat gca aaa ggt cat cat gta gtg cca ggt ttt      192
Lys Ile Gln Val Ile Asp Ala Lys Gly His His Val Val Pro Gly Phe
     50                  55                  60 atc gat ata cat att cat ggt ggt tat gga cag gat gca atg gat ggg      240
Ile Asp Ile His Ile His Gly Gly Tyr Gly Gln Asp Ala Met Asp Gly
 65                  70                  75                  80 tca cac gat ggc tta aaa tat cta tcc gaa aat ttg ttg tct gaa ggg      288
Ser His Asp Gly Leu Lys Tyr Leu Ser Glu Asn Leu Leu Ser Glu Gly
                 85                  90                  95 acg aca tca tac ttg gcc act aca atg acg caa tcg act gat aaa ata      336
Thr Thr Ser Tyr Leu Ala Thr Thr Met Thr Gln Ser Thr Asp Lys Ile
            100                 105                 110 gat aaa gca ctt ata aat att gct aaa tat gaa gtg gag caa gat gtt      384
Asp Lys Ala Leu Ile Asn Ile Ala Lys Tyr Glu Val Glu Gln Asp Val
            115                 120                 125 cac aat gca gcg gaa att gta ggt ata cat ttg gaa ggg cca ttt ata      432
His Asn Ala Ala Glu Ile Val Gly Ile His Leu Glu Gly Pro Phe Ile
        130                 135                 140 tct gaa aat aaa gtt ggt gct caa cat ccg caa tac gtt gta cgc cca      480
Ser Glu Asn Lys Val Gly Ala Gln His Pro Gln Tyr Val Val Arg Pro
145                 150                 155                 160
```

-continued

```
ttt atc gat aaa att aaa cat ttt caa gag act gct aac gga cta ata      528
Phe Ile Asp Lys Ile Lys His Phe Gln Glu Thr Ala Asn Gly Leu Ile
            165                 170                 175 aag att atg acg ttt gca cct gaa gtt gaa ggt gca aaa gaa gcg ctt      576
Lys Ile Met Thr Phe Ala Pro Glu Val Glu Gly Ala Lys Glu Ala Leu
        180                 185                 190 gaa acg tat aaa gat gac att att ttt tca att ggt cat aca gtg gca      624
Glu Thr Tyr Lys Asp Asp Ile Ile Phe Ser Ile Gly His Thr Val Ala
            195                 200                 205 aca tac gaa gaa gca gtt gaa gct gtt gag cga gga gct aaa cat gtc      672
Thr Tyr Glu Glu Ala Val Glu Ala Val Glu Arg Gly Ala Lys His Val
        210                 215                 220 acg cac tta tat aat gca gcg acg cca ttc caa cat aga gaa cca ggt      720
Thr His Leu Tyr Asn Ala Ala Thr Pro Phe Gln His Arg Glu Pro Gly
225                 230                 235                 240 gtt ttt gta gca gga tgg ttg aat gat gct cta cat acc gaa atg att      768
Val Phe Val Ala Gly Trp Leu Asn Asp Ala Leu His Thr Glu Met Ile
            245                 250                 255 gtt gat ggc aca cat tct cat ccg gca tcg gtt gca att gct tac cgt      816
Val Asp Gly Thr His Ser His Pro Ala Ser Val Ala Ile Ala Tyr Arg
        260                 265                 270 atg aaa ggt aat gaa cgt ttt tat tta att acc gat gca atg cgt gca      864
Met Lys Gly Asn Glu Arg Phe Tyr Leu Ile Thr Asp Ala Met Arg Ala
            275                 280                 285 aaa ggt atg cct gaa gga gaa tat gat ttg ggt gga caa aaa gta act      912
Lys Gly Met Pro Glu Gly Glu Tyr Asp Leu Gly Gly Gln Lys Val Thr
        290                 295                 300 gtt caa tcg caa caa gca cgt ctt gca aat ggt gcg ctt gct ggt agt      960
Val Gln Ser Gln Gln Ala Arg Leu Ala Asn Gly Ala Leu Ala Gly Ser
305                 310                 315                 320 att tta aaa atg aat cat ggg tta cgt aac tta ata tca ttt aca ggt     1008
Ile Leu Lys Met Asn His Gly Leu Arg Asn Leu Ile Ser Phe Thr Gly
            325                 330                 335 gat aca tta gat cat tta tgg cga gta aca agt tta aat caa gcc att     1056
Asp Thr Leu Asp His Leu Trp Arg Val Thr Ser Leu Asn Gln Ala Ile
        340                 345                 350 gca tta ggt atc gat gat aga aaa ggt agt att aaa gta aat aag gat     1104
Ala Leu Gly Ile Asp Asp Arg Lys Gly Ser Ile Lys Val Asn Lys Asp
            355                 360                 365 gca gat ctt gtt att cta gat gat gac atg aat gta aaa tct aca ata     1152
Ala Asp Leu Val Ile Leu Asp Asp Asp Met Asn Val Lys Ser Thr Ile
        370                 375                 380 aaa caa ggt aag gtt cac aca ttt agc taa                             1182
Lys Gln Gly Lys Val His Thr Phe Ser
385                 390
```

<210> SEQ ID NO 9
<211> LENGTH: 424
<212> TYPE: DNA
<213> ORGANISM: Staphylococcus aureus
<220> FEATURE:
<221> NAME/KEY: CDS
<222> LOCATION: (1)...(423)

<400> SEQUENCE: 9

```
gaa gat gac gcc ttg ata aat cga atg ggc ttc aat aat att ggt atg       48
Glu Asp Asp Ala Leu Ile Asn Arg Met Gly Phe Asn Asn Ile Gly Met
1               5                   10                  15 aac aaa gca ctc agt cat ttg cgt aaa aat gct tat caa gta cct gtt       96
Asn Lys Ala Leu Ser His Leu Arg Lys Asn Ala Tyr Gln Val Pro Val
            20                  25                  30
```

```
ggt atc aat gtt ggt gtg aat aaa atg aca cct tat gaa gcg cgt tat       144
Gly Ile Asn Val Gly Val Asn Lys Met Thr Pro Tyr Glu Ala Arg Tyr
        35                  40                  45 caa gat tat ata aaa gtc att gat acg ttt aaa cac gac gtt tca ttt       192
Gln Asp Tyr Ile Lys Val Ile Asp Thr Phe Lys His Asp Val Ser Phe
50                  55                  60 ttc aca gtc aat atc agt tct cca aat act gaa aac ctt caa aat ttc       240
Phe Thr Val Asn Ile Ser Ser Pro Asn Thr Glu Asn Leu Gln Asn Phe
65                  70                  75                  80 cat gat aaa gat gaa ttt tca atg tta tgt caa gct ttg aca aca ttt       288
His Asp Lys Asp Glu Phe Ser Met Leu Cys Gln Ala Leu Thr Thr Phe
                85                  90                  95 aaa aaa cag cac gat gta aca gtg cca att tac tta aaa cta acg tct       336
Lys Lys Gln His Asp Val Thr Val Pro Ile Tyr Leu Lys Leu Thr Ser
            100                 105                 110 gat atg gat ttc gat ggc tta aaa gca cta tta cca gcg att act gag       384
Asp Met Asp Phe Asp Gly Leu Lys Ala Leu Leu Pro Ala Ile Thr Glu
        115                 120                 125 aca ttt gac ggt atc atc tta gca aac aca acg ctc gtg c                 424
Thr Phe Asp Gly Ile Ile Leu Ala Asn Thr Thr Leu Val
130                 135                 140

<210> SEQ ID NO 10
<211> LENGTH: 1071
<212> TYPE: DNA
<213> ORGANISM: Staphylococcus aureus
<220> FEATURE:
<221> NAME/KEY: CDS
<222> LOCATION: (1)...(1068)

<400> SEQUENCE: 10 atg tac aaa tta att aaa cct ttc tta ttc aaa atc gaa ccc gaa aaa        48
Met Tyr Lys Leu Ile Lys Pro Phe Leu Phe Lys Ile Glu Pro Glu Lys
1               5                   10                  15 gca cac gga cta act atc gat gca tta aaa acg tta caa aaa ttt cca        96
Ala His Gly Leu Thr Ile Asp Ala Leu Lys Thr Leu Gln Lys Phe Pro
            20                  25                  30 gtt tta ttc cca gtc gtc gat aaa cta ttt act tat aag aat cca acg       144
Val Leu Phe Pro Val Val Asp Lys Leu Phe Thr Tyr Lys Asn Pro Thr
        35                  40                  45 tta tca caa acg ata caa ggt aat acg tat gac aat cca att ggc tta       192
Leu Ser Gln Thr Ile Gln Gly Asn Thr Tyr Asp Asn Pro Ile Gly Leu
50                  55                  60 gca gct ggt ttc gac aaa tct tgc gaa gta cca aaa gca ttg gaa cac       240
Ala Ala Gly Phe Asp Lys Ser Cys Glu Val Pro Lys Ala Leu Glu His
65                  70                  75                  80 ctt gga ttc ggt gct tta gaa tta ggt ggt atc aca cct aaa cct caa       288
Leu Gly Phe Gly Ala Leu Glu Leu Gly Gly Ile Thr Pro Lys Pro Gln
                85                  90                  95 ccg ggt aac cct caa ccg cgc atg ttc aga tta tta gaa gat gac gcc       336
Pro Gly Asn Pro Gln Pro Arg Met Phe Arg Leu Leu Glu Asp Asp Ala
            100                 105                 110 ttg ata aat cga atg ggc ttc aat aat att ggt atg aac aaa gca ctc       384
Leu Ile Asn Arg Met Gly Phe Asn Asn Ile Gly Met Asn Lys Ala Leu
        115                 120                 125 agt cat ttg cgt aaa aat gct tat caa gta cct gtt ggt atc aat gtt       432
Ser His Leu Arg Lys Asn Ala Tyr Gln Val Pro Val Gly Ile Asn Val
130                 135                 140 ggt gtg aat aaa atg aca cct tat gaa gcg cgt tat caa gat tat ata       480
Gly Val Asn Lys Met Thr Pro Tyr Glu Ala Arg Tyr Gln Asp Tyr Ile
145                 150                 155                 160
```

-continued

```
aaa gtc att gat acg ttt aaa cac gac gtt tca ttt ttc aca gtc aat         528
Lys Val Ile Asp Thr Phe Lys His Asp Val Ser Phe Phe Thr Val Asn
            165                 170                 175 atc agt tct cca aat act gaa aac ctt caa aat ttc cat gat aaa gat         576
Ile Ser Ser Pro Asn Thr Glu Asn Leu Gln Asn Phe His Asp Lys Asp
        180                 185                 190 gaa ttt tca atg tta tgt caa gct ttg aca aca ttt aaa aaa cag cac         624
Glu Phe Ser Met Leu Cys Gln Ala Leu Thr Thr Phe Lys Lys Gln His
    195                 200                 205 gat gta aca gtg cca att tac tta aaa cta acg tct gat atg gat ttc         672
Asp Val Thr Val Pro Ile Tyr Leu Lys Leu Thr Ser Asp Met Asp Phe
210                 215                 220 gat ggc tta aaa gca cta tta cca gcg att act gag aca ttt gac ggt         720
Asp Gly Leu Lys Ala Leu Leu Pro Ala Ile Thr Glu Thr Phe Asp Gly
225                 230                 235                 240 atc atc tta gca aac aca acg ctc gtg cga caa cga gat ggt tta act         768
Ile Ile Leu Ala Asn Thr Thr Leu Val Arg Gln Arg Asp Gly Leu Thr
            245                 250                 255 tct gct aat aaa gtc gaa gaa ggc ggt ttg agt ggt cgt cca tta ttt         816
Ser Ala Asn Lys Val Glu Glu Gly Gly Leu Ser Gly Arg Pro Leu Phe
        260                 265                 270 gaa cgt aat tta aaa ttg att aag tat gct tat cag caa aca aat ggt         864
Glu Arg Asn Leu Lys Leu Ile Lys Tyr Ala Tyr Gln Gln Thr Asn Gly
    275                 280                 285 gaa ttt tta att ata ggt aca ggc ggc gta ttc agt act gaa gat gca         912
Glu Phe Leu Ile Ile Gly Thr Gly Gly Val Phe Ser Thr Glu Asp Ala
290                 295                 300 atc aaa atg atg cgt cac ggt gcg tca ctt att caa att tat tca cca         960
Ile Lys Met Met Arg His Gly Ala Ser Leu Ile Gln Ile Tyr Ser Pro
305                 310                 315                 320 ctt gtt att gaa ggc cca ggt tta act aag aaa atg aac aaa ggc atc        1008
Leu Val Ile Glu Gly Pro Gly Leu Thr Lys Lys Met Asn Lys Gly Ile
            325                 330                 335 gca cgt tac tta aaa gat cat cat ttt gac aat gtc agt gat att ata        1056
Ala Arg Tyr Leu Lys Asp His His Phe Asp Asn Val Ser Asp Ile Ile
        340                 345                 350 gga cta gat gcc taa                                                    1071
Gly Leu Asp Ala
    355
```

<210> SEQ ID NO 11
<211> LENGTH: 295
<212> TYPE: PRT
<213> ORGANISM: Staphylococcus aureus
<220> FEATURE:
<221> NAME/KEY: VARIANT
<222> LOCATION: (1)...(295)
<223> OTHER INFORMATION: Xaa = Any Amino Acid

<400> SEQUENCE: 11

```
Met Glu Thr Ile Ile Glu Glu Tyr Leu Arg Phe Ile Gln Ile Glu Lys
1               5                   10                  15

Gly Leu Ser Ser Asn Thr Ile Gly Ala Tyr Arg Arg Asp Leu Lys Lys
            20                  25                  30

Tyr Gln Asp Tyr Met Thr Glu His His Ile Ser His Ile Asp Phe Ile
        35                  40                  45

Asp Arg Gln Leu Ile Gln Glu Cys Leu Gly His Leu Ile Asp Gln Gly
    50                  55                  60

Gln Ser Ala Lys Ser Ile Glu Arg Phe Ile Ser Thr Ile Arg Ser Phe
65                  70                  75                  80
```

```
His Gln Phe Ala Ile Arg Glu Lys Tyr Ala Ala Lys Asp Pro Thr Val
                85                  90                  95
Leu Leu Asp Ser Pro Lys Tyr Asp Lys Lys Leu Pro Asp Val Leu Asn
            100                 105                 110
Val Asp Glu Val Leu Ala Leu Leu Glu Thr Pro Asp Leu Asn Lys Ile
        115                 120                 125
Asn Gly Tyr Arg Asp Arg Thr Met Leu Glu Leu Leu Tyr Ala Thr Gly
    130                 135                 140
Met Arg Val Ser Glu Leu Ile His Leu Glu Leu Glu Asn Val Asn Leu
145                 150                 155                 160
Ile Met Gly Phe Val Arg Val Phe Gly Lys Gly Asp Lys Glu Arg Ile
                165                 170                 175
Val Pro Leu Gly Asp Ala Val Ile Glu Tyr Leu Thr Thr Tyr Ile Glu
            180                 185                 190
Thr Ile Arg Pro Gln Leu Leu Lys Lys Thr Val Thr Glu Val Leu Phe
        195                 200                 205
Leu Asn Met His Gly Lys Pro Leu Ser Arg Gln Ala Ile Trp Lys Met
    210                 215                 220
Ile Lys Gln Asn Gly Val Lys Ala Asn Ile Lys Lys Leu Thr Pro
225                 230                 235                 240
His Thr Leu Arg His Ser Phe Ala Thr His Leu Leu Glu Asn Gly Ala
                245                 250                 255
Asp Leu Arg Ala Val Xaa Glu Met Leu Gly His Ser Asp Ile Ser Thr
            260                 265                 270
Thr Gln Leu Tyr Thr His Val Ser Lys Ser Gln Ile Lys Lys Met Tyr
        275                 280                 285
Tyr Pro Phe His Pro Lys Thr
    290                 295

<210> SEQ ID NO 12
<211> LENGTH: 390
<212> TYPE: PRT
<213> ORGANISM: Staphylococcus aureus

<400> SEQUENCE: 12

Met Thr Leu Ser Lys Glu Thr Glu Val Ile Phe Asp Trp Arg Arg Gly
1               5                   10                  15
Val Glu Tyr His Ser Ala Asn Pro Pro Leu Tyr Asp Phe Ser Thr Phe
            20                  25                  30
His Gln Thr Ser Leu Gly Gly Asp Val Lys Tyr Asp Tyr Ala Arg Ser
        35                  40                  45
Gly Asn Pro Asn Arg Glu Leu Leu Glu Glu Lys Leu Ala Arg Leu Glu
    50                  55                  60
Gln Gly Lys Phe Ala Phe Ala Phe Ala Ser Gly Ile Ala Ala Ile Ser
65                  70                  75                  80
Ala Val Leu Leu Thr Phe Lys Ser Gly Asp His Val Ile Leu Pro Asp
                85                  90                  95
Asp Val Tyr Gly Gly Thr Phe Arg Leu Thr Glu Gln Ile Leu Asn Arg
            100                 105                 110
Phe Asn Ile Glu Phe Thr Thr Val Asp Thr Thr Lys Leu Glu Gln Ile
        115                 120                 125
Glu Gly Ala Ile Gln Ser Asn Thr Lys Leu Ile Tyr Ile Glu Thr Pro
    130                 135                 140
Ser Asn Pro Cys Phe Lys Ile Thr Asp Ile Lys Ala Val Ser Lys Ile
```

```
145                 150                 155                 160
Ala Glu Lys His Glu Leu Leu Val Ala Val Asp Asn Thr Phe Met Thr
                165                 170                 175

Pro Leu Gly Gln Ser Pro Leu Leu Gly Ala Asp Ile Val Ile His
                180                 185                 190

Ser Ala Thr Lys Phe Leu Ser Gly His Ser Asp Leu Ile Ala Gly Ala
                195                 200                 205

Val Ile Thr Asn Ile Glu Pro Ile Ser Glu Ala Leu Tyr Leu Asn His
                210                 215                 220

Asn Gly Thr Gly Asn Met Leu Ser Ala Gln Asp Ser Trp Thr Leu Ala
225                 230                 235                 240

Lys His Leu Lys Thr Phe Pro Ile Arg Phe Lys Gln Ser Val Glu Asn
                245                 250                 255

Ala Gln Lys Ile Val Ser Phe Leu Ile Lys Gln Asp Glu Ile Ser Glu
                260                 265                 270

Val Tyr Tyr Pro Gly Leu Thr Thr Ala His Leu Glu Gln Ala Lys Asn
                275                 280                 285

Gly Gly Ala Val Ile Gly Phe Arg Leu Ala Asp Glu Ser Lys Ala Gln
                290                 295                 300

Gln Phe Val Asp Ala Leu Thr Leu Pro Leu Val Ser Val Ser Leu Gly
305                 310                 315                 320

Gly Val Glu Thr Ile Leu Ser His Pro Ala Thr Met Ser His Ala Ala
                325                 330                 335

Leu Pro Glu Glu Val Arg Gln Glu Arg Gly Ile Thr Phe Gly Leu Phe
                340                 345                 350

Arg Leu Ser Val Gly Leu Glu Asp Pro Asp Glu Leu Ile Ala Asp Ile
                355                 360                 365

Lys Tyr Ala Leu Lys Glu Ala Ser Asn Glu Ser Ile Pro Ser His Asn
                370                 375                 380

Cys Lys Ile Met Phe Lys
385                 390

<210> SEQ ID NO 13
<211> LENGTH: 455
<212> TYPE: PRT
<213> ORGANISM: Staphylococcus aureus
<220> FEATURE:
<221> NAME/KEY: VARIANT
<222> LOCATION: (1)...(455)
<223> OTHER INFORMATION: Xaa = Any Amino Acid

<400> SEQUENCE: 13

Ser Pro Ser Leu Phe His Lys Ser Gln Thr Met Thr Thr Pro Met Leu
1               5                   10                  15

Ser Leu Gly Asn Ala Phe Asn Glu Asp Asp Leu Arg Lys Phe Asp Gln
                20                  25                  30

Arg Ile Arg Glu Gln Ile Gly Asn Val Glu Tyr Met Cys Glu Leu Lys
            35                  40                  45

Ile Asp Gly Leu Ala Val Ser Leu Lys Tyr Val Asp Gly Tyr Phe Val
        50                  55                  60

Gln Gly Leu Thr Arg Gly Asp Gly Thr Thr Gly Glu Asp Ile Thr Glu
65                  70                  75                  80

Asn Leu Lys Thr Ile His Ala Ile Pro Leu Lys Met Lys Glu Pro Leu
                85                  90                  95

Asn Val Glu Val Arg Gly Glu Ala Tyr Met Pro Arg Arg Ser Phe Leu
                100                 105                 110
```

```
Arg Leu Asn Glu Glu Lys Glu Lys Asn Asp Gln Leu Phe Ala Asn
        115                 120                 125
Pro Arg Asn Ala Ala Gly Ser Leu Arg Gln Leu Asp Ser Lys Leu
    130                 135                 140
Thr Ala Lys Arg Lys Leu Ser Val Phe Ile Tyr Ser Val Asn Asp Phe
145                 150                 155                 160
Thr Asp Phe Asn Ala Arg Ser Gln Ser Glu Ala Leu Asp Glu Leu Asp
                165                 170                 175
Lys Leu Gly Phe Thr Thr Asn Lys Asn Arg Ala Arg Val Asn Asn Ile
            180                 185                 190
Asp Gly Val Leu Glu Tyr Ile Glu Lys Trp Thr Ser Gln Arg Glu Ser
            195                 200                 205
Leu Pro Tyr Asp Ile Asp Gly Ile Val Ile Lys Val Asn Asp Leu Asp
    210                 215                 220
Gln Gln Asp Glu Met Gly Phe Thr Gln Lys Ser Pro Arg Trp Ala Ile
225                 230                 235                 240
Ala Tyr Lys Phe Pro Ala Glu Glu Val Val Thr Lys Leu Leu Asp Ile
                245                 250                 255
Glu Leu Ser Ile Gly Arg Thr Gly Val Val Thr Pro Thr Ala Ile Leu
            260                 265                 270
Glu Pro Val Lys Val Ala Gly Thr Thr Val Ser Arg Ala Ser Leu His
            275                 280                 285
Asn Glu Asp Leu Ile His Asp Arg Asp Ile Arg Ile Gly Asp Ser Val
    290                 295                 300
Val Val Lys Lys Ala Gly Asp Ile Ile Pro Glu Val Val Arg Ser Ile
305                 310                 315                 320
Pro Glu Arg Arg Pro Glu Asp Ala Val Thr Tyr His Met Pro Thr His
                325                 330                 335
Cys Pro Ser Cys Gly His Glu Leu Val Arg Ile Glu Gly Glu Val Ala
            340                 345                 350
Leu Arg Cys Ile Asn Pro Lys Cys Gln Ala Gln Leu Val Glu Gly Leu
    355                 360                 365
Ile His Phe Val Ser Arg Gln Ala Met Asn Ile Asp Gly Leu Gly Thr
370                 375                 380
Lys Ile Ile Gln Gln Leu Tyr Gln Ser Glu Leu Ile Lys Asp Val Ala
385                 390                 395                 400
Asp Ile Ser Tyr Leu Thr Glu Gly Asp Leu Leu Pro Leu Asp Arg Met
                405                 410                 415
Ala Gln Lys Lys Val Asp Asn Leu Leu Ala Ala Ile Gln Gln Ala Lys
            420                 425                 430
Asp Asn Ser Xaa Glu Asn Leu Leu Phe Gly Leu Gly Ile Arg His Leu
            435                 440                 445
Gly Val Lys Ala Ser Lys Cys
    450                 455

<210> SEQ ID NO 14
<211> LENGTH: 329
<212> TYPE: PRT
<213> ORGANISM: Staphylococcus aureus

<400> SEQUENCE: 14

Met Thr Val Thr Ile Tyr Asp Val Ala Arg Glu Ala Arg Val Ser Met
1               5                   10                  15
Ala Thr Val Ser Arg Val Val Asn Gly Asn Gln Asn Val Lys Ala Glu
```

```
                    20                  25                  30
Thr Lys Asn Lys Val Asn Glu Val Ile Lys Arg Leu Asn Tyr Arg Pro
            35                  40                  45
Asn Ala Val Ala Arg Gly Leu Ala Ser Lys Lys Thr Thr Thr Val Gly
        50                  55                  60
Val Ile Ile Pro Asp Ile Ser Asn Ile Tyr Tyr Ser Gln Leu Ala Arg
65                  70                  75                  80
Gly Leu Glu Asp Ile Ala Thr Met Tyr Lys Tyr His Ser Ile Ile Ser
                85                  90                  95
Asn Ser Asp Asn Asp Pro Glu Lys Glu Lys Glu Ile Phe Asn Asn Leu
            100                 105                 110
Leu Ser Lys Gln Val Asp Gly Ile Ile Phe Leu Gly Gly Thr Ile Thr
        115                 120                 125
Glu Glu Met Lys Glu Leu Ile Asn Gln Ser Ser Val Pro Val Val Val
    130                 135                 140
Ser Gly Thr Asn Gly Lys Asp Ala His Ile Ala Ser Val Asn Ile Asp
145                 150                 155                 160
Phe Thr Glu Ala Ala Lys Glu Ile Thr Gly Glu Leu Ile Glu Lys Gly
                165                 170                 175
Ala Lys Ser Phe Ala Leu Val Gly Gly Glu His Ser Lys Lys Ala Gln
            180                 185                 190
Glu Asp Val Leu Glu Gly Leu Thr Glu Val Leu Asn Lys Asn Gly Leu
        195                 200                 205
Gln Leu Gly Asp Thr Leu Asn Cys Ser Gly Ala Glu Ser Tyr Lys Glu
    210                 215                 220
Gly Val Lys Ala Phe Ala Lys Met Lys Gly Asn Leu Pro Asp Ala Ile
225                 230                 235                 240
Leu Cys Ile Ser Asp Glu Glu Ala Ile Gly Ile Met His Ser Ala Met
                245                 250                 255
Asp Ala Gly Ile Lys Val Pro Glu Glu Leu Gln Ile Ile Ser Phe Asn
            260                 265                 270
Asn Thr Arg Leu Val Glu Met Val Arg Pro Gln Leu Ser Ser Val Ile
        275                 280                 285
Gln Pro Leu Tyr Asp Ile Gly Ala Val Gly Met Arg Leu Leu Thr Lys
    290                 295                 300
Tyr Met Asn Asp Glu Lys Ile Gln Glu Pro Asn Val Val Leu Pro His
305                 310                 315                 320
Arg Ile Glu Tyr Arg Gly Thr Thr Lys
                325

<210> SEQ ID NO 15
<211> LENGTH: 69
<212> TYPE: PRT
<213> ORGANISM: Staphylococcus aureus

<400> SEQUENCE: 15

Ile Lys Arg Met Asp Val Asp Asn Met Ser Asp Tyr Lys Leu Lys Ile
1               5                   10                  15
Ile Glu Leu Ile Lys Ser Asp Ile Thr Gly Tyr Gln Ile His Lys Gln
            20                  25                  30
Thr Gly Val Ala Gln Tyr Val Ile Ser Gln Leu Arg Gln Gly Lys Arg
        35                  40                  45
Glu Val Asp Asn Leu Thr Leu Asn Thr Thr Glu Lys Leu Tyr Ser Tyr
    50                  55                  60
```

Ala Arg Gln Val Leu
65

<210> SEQ ID NO 16
<211> LENGTH: 388
<212> TYPE: PRT
<213> ORGANISM: Staphylococcus aureus

<400> SEQUENCE: 16

Met Ile Asn Glu Arg Glu Val Phe Ile Leu Ile Tyr Leu Asp Asn Ala
1               5                   10                  15

Ala Thr Thr Lys Ala Phe Asp Glu Val Leu Asp Thr Tyr Val Lys Val
            20                  25                  30

Asn Gln Ser Met Tyr Val Asn Pro Asn Ser Pro His Lys Ala Gly Ser
        35                  40                  45

Gln Ala Asn Gln Leu Leu Gln Gln Ala Lys Ala Gln Ile Asn Ala Met
    50                  55                  60

Ile Asn Ser Lys Thr Asn Tyr Asp Val Val Phe Thr Ser Gly Ala Thr
65                  70                  75                  80

Glu Ser Asn Asn Leu Ala Leu Lys Gly Ile Ala Tyr Arg Lys Phe Asp
                85                  90                  95

Thr Ala Lys Glu Ile Ile Thr Ser Val Leu Glu His Pro Ser Val Leu
            100                 105                 110

Glu Val Val Arg Tyr Leu Glu Ala His Glu Gly Phe Lys Val Lys Tyr
        115                 120                 125

Val Asp Val Lys Lys Asp Gly Ser Ile Asn Leu Glu His Phe Lys Glu
    130                 135                 140

Leu Val Ser Asp Lys Val Gly Leu Val Thr Cys Met Tyr Val Asn Asn
145                 150                 155                 160

Val Thr Gly Gln Ile Gln Pro Ile Pro Gln Met Ala Lys Val Ile Lys
                165                 170                 175

Asn Tyr Pro Lys Ala His Phe His Val Asp Ala Ala Gln Ala Phe Gly
            180                 185                 190

Lys Ile Ser Met Asp Leu Asn Asn Ile Asp Ser Ile Ser Leu Ser Gly
        195                 200                 205

His Lys Phe Asn Gly Leu Lys Gly Gln Gly Val Leu Leu Val Asn His
    210                 215                 220

Ile Gln Asn Val Gly Pro Ser Val His Gly Gly Gln Glu Tyr Gly
225                 230                 235                 240

Val Arg Ser Gly Thr Val Asn Leu Pro Asn Asp Ile Ala Met Val Lys
                245                 250                 255

Ala Met Lys Ile Ala Asn Glu Asn Phe Glu Ala Leu Asn Ala Phe Val
            260                 265                 270

Thr Glu Leu Asn Asn Asp Val Arg Gln Phe Leu Asn Lys Tyr His Gly
        275                 280                 285

Val Tyr Ile Asn Ser Ser Thr Ser Gly Ser Pro Phe Val Leu Asn Ile
    290                 295                 300

Ser Phe Pro Gly Val Lys Gly Glu Val Leu Val Asn Ala Phe Ser Lys
305                 310                 315                 320

Tyr Asp Ile Met Ile Ser Thr Thr Ser Ala Cys Ser Ser Lys Arg Asn
                325                 330                 335

Lys Leu Asn Glu Val Leu Ala Ala Met Gly Leu Ser Asp Lys Ser Ile
            340                 345                 350

Glu Gly Ser Ile Arg Leu Ser Phe Gly Ala Thr Thr Lys Glu Asp
        355                 360                 365

```
Ile Ala Arg Phe Lys Glu Ile Phe Ile Ile Ile Tyr Glu Glu Ile Lys
        370                 375                 380

Glu Leu Leu Lys
385

<210> SEQ ID NO 17
<211> LENGTH: 179
<212> TYPE: PRT
<213> ORGANISM: Staphylococcus aureus

<400> SEQUENCE: 17

Leu Leu Leu Phe Gly Asn Asp Ala Leu Met Pro Asn Leu Phe Gln Tyr
1               5                   10                  15

Ile Leu Asp Ile His Leu Glu Leu Leu His Pro Ile Gln Cys Asn Ser
            20                  25                  30

Arg Arg Ala Asn Ile Gly Phe Ser Met Leu Pro Ala Ser Met Ala Pro
        35                  40                  45

Ser Val Leu Pro Ala Pro Thr Ser Ile Trp Ile Ser Ile Asn Asn
    50                  55                  60

Ile Ile Leu Pro Ser Asp Ser Leu Thr Ser Phe Arg Thr Ala Phe Asn
65                  70                  75                  80

Leu Ser Ser Asn Ser Pro Arg Tyr Leu Ala Pro Ala Thr Asn Ala Leu
                85                  90                  95

Lys Ser Asn Ser Lys Thr Val Leu Ser Asn Asn Asp Ser Gly Thr Ser
            100                 105                 110

Phe Leu Thr Ile Arg Cys Ala Asn Pro Ser Thr Ile Ala Val Leu Pro
        115                 120                 125

Thr Pro Gly Ser Pro Met Ser Thr Gly Leu Phe Leu Val Leu Arg Leu
    130                 135                 140

Lys Ile Arg Ile Val Phe Arg Ile Ser Ser Ser Leu Pro Ile Thr Gly
145                 150                 155                 160

Ser Ile Leu Pro Cys Leu Thr Ser Ser Thr Lys Ser Arg Pro Tyr Leu
                165                 170                 175

Ala Arg Ala

<210> SEQ ID NO 18
<211> LENGTH: 393
<212> TYPE: PRT
<213> ORGANISM: Staphylococcus aureus

<400> SEQUENCE: 18

Val Ser Glu Leu Ile Ile Tyr Asn Gly Lys Val Tyr Thr Glu Asp Gly
1               5                   10                  15

Lys Ile Asp Asn Gly Tyr Ile His Val Lys Asp Gly Gln Ile Val Ala
            20                  25                  30

Ile Gly Glu Val Asn Asp Lys Ala Ala Ile Asp Asn Asp Thr Thr Asn
        35                  40                  45

Lys Ile Gln Val Ile Asp Ala Lys Gly His His Val Val Pro Gly Phe
    50                  55                  60

Ile Asp Ile His Ile His Gly Gly Tyr Gly Gln Asp Ala Met Asp Gly
65                  70                  75                  80

Ser His Asp Gly Leu Lys Tyr Leu Ser Glu Asn Leu Leu Ser Glu Gly
                85                  90                  95

Thr Thr Ser Tyr Leu Ala Thr Met Thr Gln Ser Thr Asp Lys Ile
            100                 105                 110
```

```
Asp Lys Ala Leu Ile Asn Ile Ala Lys Tyr Glu Val Glu Gln Asp Val
        115                 120                 125

His Asn Ala Ala Glu Ile Val Gly Ile His Leu Glu Gly Pro Phe Ile
        130                 135                 140

Ser Glu Asn Lys Val Gly Ala Gln His Pro Gln Tyr Val Val Arg Pro
145                 150                 155                 160

Phe Ile Asp Lys Ile Lys His Phe Gln Glu Thr Ala Asn Gly Leu Ile
                165                 170                 175

Lys Ile Met Thr Phe Ala Pro Glu Val Glu Gly Ala Lys Glu Ala Leu
            180                 185                 190

Glu Thr Tyr Lys Asp Asp Ile Ile Phe Ser Ile Gly His Thr Val Ala
        195                 200                 205

Thr Tyr Glu Glu Ala Val Glu Ala Val Glu Arg Gly Ala Lys His Val
        210                 215                 220

Thr His Leu Tyr Asn Ala Ala Thr Pro Phe Gln His Arg Glu Pro Gly
225                 230                 235                 240

Val Phe Val Ala Gly Trp Leu Asn Asp Ala Leu His Thr Glu Met Ile
                245                 250                 255

Val Asp Gly Thr His Ser His Pro Ala Ser Val Ala Ile Ala Tyr Arg
            260                 265                 270

Met Lys Gly Asn Glu Arg Phe Tyr Leu Ile Thr Asp Ala Met Arg Ala
        275                 280                 285

Lys Gly Met Pro Glu Gly Glu Tyr Asp Leu Gly Gln Lys Val Thr
        290                 295                 300

Val Gln Ser Gln Gln Ala Arg Leu Ala Asn Gly Ala Leu Ala Gly Ser
305                 310                 315                 320

Ile Leu Lys Met Asn His Gly Leu Arg Asn Leu Ile Ser Phe Thr Gly
                325                 330                 335

Asp Thr Leu Asp His Leu Trp Arg Val Thr Ser Leu Asn Gln Ala Ile
            340                 345                 350

Ala Leu Gly Ile Asp Asp Arg Lys Gly Ser Ile Lys Val Asn Lys Asp
        355                 360                 365

Ala Asp Leu Val Ile Leu Asp Asp Met Asn Val Lys Ser Thr Ile
370                 375                 380

Lys Gln Gly Lys Val His Thr Phe Ser
385                 390

<210> SEQ ID NO 19
<211> LENGTH: 142
<212> TYPE: PRT
<213> ORGANISM: Staphylococcus aureus

<400> SEQUENCE: 19

Glu Asp Asp Ala Leu Ile Asn Arg Met Gly Phe Asn Asn Ile Gly Met
1               5                   10                  15

Asn Lys Ala Leu Ser His Leu Arg Lys Asn Ala Tyr Gln Val Pro Val
            20                  25                  30

Gly Ile Asn Val Gly Val Asn Lys Met Thr Pro Tyr Glu Ala Arg Tyr
        35                  40                  45

Gln Asp Tyr Ile Lys Val Ile Asp Thr Phe Lys His Asp Val Ser Phe
    50                  55                  60

Phe Thr Val Asn Ile Ser Ser Pro Asn Thr Glu Asn Leu Gln Asn Phe
65                  70                  75                  80

His Asp Lys Asp Glu Phe Ser Met Leu Cys Gln Ala Leu Thr Thr Phe
                85                  90                  95
```

```
Lys Lys Gln His Asp Val Thr Val Pro Ile Tyr Leu Lys Leu Thr Ser
            100                 105                 110

Asp Met Asp Phe Asp Gly Leu Lys Ala Leu Leu Pro Ala Ile Thr Glu
            115                 120                 125

Thr Phe Asp Gly Ile Ile Leu Ala Asn Thr Thr Leu Val Xaa
            130                 135                 140

<210> SEQ ID NO 20
<211> LENGTH: 356
<212> TYPE: PRT
<213> ORGANISM: Staphylococcus aureus

<400> SEQUENCE: 20

Met Tyr Lys Leu Ile Lys Pro Phe Leu Phe Lys Ile Glu Pro Glu Lys
  1               5                  10                  15

Ala His Gly Leu Thr Ile Asp Ala Leu Lys Thr Leu Gln Lys Phe Pro
             20                  25                  30

Val Leu Phe Pro Val Val Asp Lys Leu Phe Thr Tyr Lys Asn Pro Thr
             35                  40                  45

Leu Ser Gln Thr Ile Gln Gly Asn Thr Tyr Asp Asn Pro Ile Gly Leu
         50                  55                  60

Ala Ala Gly Phe Asp Lys Ser Cys Glu Val Pro Lys Ala Leu Glu His
 65                  70                  75                  80

Leu Gly Phe Gly Ala Leu Glu Leu Gly Gly Ile Thr Pro Lys Pro Gln
                 85                  90                  95

Pro Gly Asn Pro Gln Pro Arg Met Phe Arg Leu Leu Glu Asp Asp Ala
            100                 105                 110

Leu Ile Asn Arg Met Gly Phe Asn Asn Ile Gly Met Asn Lys Ala Leu
            115                 120                 125

Ser His Leu Arg Lys Asn Ala Tyr Gln Val Pro Val Gly Ile Asn Val
            130                 135                 140

Gly Val Asn Lys Met Thr Pro Tyr Glu Ala Arg Tyr Gln Asp Tyr Ile
145                 150                 155                 160

Lys Val Ile Asp Thr Phe Lys His Asp Val Ser Phe Thr Val Asn
                165                 170                 175

Ile Ser Ser Pro Asn Thr Glu Asn Leu Gln Asn Phe His Asp Lys Asp
            180                 185                 190

Glu Phe Ser Met Leu Cys Gln Ala Leu Thr Thr Phe Lys Lys Gln His
            195                 200                 205

Asp Val Thr Val Pro Ile Tyr Leu Lys Leu Thr Ser Asp Met Asp Phe
            210                 215                 220

Asp Gly Leu Lys Ala Leu Leu Pro Ala Ile Thr Glu Thr Phe Asp Gly
225                 230                 235                 240

Ile Ile Leu Ala Asn Thr Thr Leu Val Arg Gln Arg Asp Gly Leu Thr
                245                 250                 255

Ser Ala Asn Lys Val Glu Glu Gly Leu Ser Gly Arg Pro Leu Phe
            260                 265                 270

Glu Arg Asn Leu Lys Leu Ile Lys Tyr Ala Tyr Gln Gln Thr Asn Gly
            275                 280                 285

Glu Phe Leu Ile Ile Gly Thr Gly Gly Val Phe Ser Thr Glu Asp Ala
            290                 295                 300

Ile Lys Met Met Arg His Gly Ala Ser Leu Ile Gln Ile Tyr Ser Pro
305                 310                 315                 320

Leu Val Ile Glu Gly Pro Gly Leu Thr Lys Lys Met Asn Lys Gly Ile
```

```
                    325                 330                 335
           Ala Arg Tyr Leu Lys Asp His His Phe Asp Asn Val Ser Asp Ile Ile
                        340                 345                 350

Gly Leu Asp Ala
                   355

<210> SEQ ID NO 21
<211> LENGTH: 22
<212> TYPE: DNA
<213> ORGANISM: Staphylococcus aureus

<400> SEQUENCE: 21
gatttatttc aacaatccgt ag                                                  22

<210> SEQ ID NO 22
<211> LENGTH: 21
<212> TYPE: DNA
<213> ORGANISM: Staphylococcus aureus

<400> SEQUENCE: 22
gtgtatagag ttgggtagta g                                                   21

<210> SEQ ID NO 23
<211> LENGTH: 20
<212> TYPE: DNA
<213> ORGANISM: Staphylococcus aureus

<400> SEQUENCE: 23
gattggagag attgtatgac                                                     20

<210> SEQ ID NO 24
<211> LENGTH: 20
<212> TYPE: DNA
<213> ORGANISM: Staphylococcus aureus

<400> SEQUENCE: 24
tccacttaaa aatttggtag                                                     20

<210> SEQ ID NO 25
<211> LENGTH: 20
<212> TYPE: DNA
<213> ORGANISM: Staphylococcus aureus

<400> SEQUENCE: 25
ttggcaacgt tgaatatatg                                                     20

<210> SEQ ID NO 26
<211> LENGTH: 21
<212> TYPE: DNA
<213> ORGANISM: Staphylococcus aureus

<400> SEQUENCE: 26
aatactacgt acaacttcag g                                                   21

<210> SEQ ID NO 27
<211> LENGTH: 20
<212> TYPE: DNA
<213> ORGANISM: Staphylococcus aureus

<400> SEQUENCE: 27
ttgattttac tgaagctgcg                                                     20
```

-continued

```
<210> SEQ ID NO 28
<211> LENGTH: 20
<212> TYPE: DNA
<213> ORGANISM: Staphylococcus aureus

<400> SEQUENCE: 28
gcaccgatat catataatgg                                                    20

<210> SEQ ID NO 29
<211> LENGTH: 19
<212> TYPE: DNA
<213> ORGANISM: Staphylococcus aureus

<400> SEQUENCE: 29
ataaaaagaa tggacgtag                                                     19

<210> SEQ ID NO 30
<211> LENGTH: 20
<212> TYPE: DNA
<213> ORGANISM: Staphylococcus aureus

<400> SEQUENCE: 30
gtaactgtat agtttttcag                                                    20

<210> SEQ ID NO 31
<211> LENGTH: 19
<212> TYPE: DNA
<213> ORGANISM: Staphylococcus aureus

<400> SEQUENCE: 31
ggaattcggc acgagcggc                                                     19

<210> SEQ ID NO 32
<211> LENGTH: 19
<212> TYPE: DNA
<213> ORGANISM: Staphylococcus aureus

<400> SEQUENCE: 32
cattttgtat gtgatttac                                                     19

<210> SEQ ID NO 33
<211> LENGTH: 19
<212> TYPE: DNA
<213> ORGANISM: Staphylococcus aureus

<400> SEQUENCE: 33
tggaaacgac gctctaatg                                                     19

<210> SEQ ID NO 34
<211> LENGTH: 20
<212> TYPE: DNA
<213> ORGANISM: Staphylococcus aureus

<400> SEQUENCE: 34
aatacgattc gtattttaag                                                    20

<210> SEQ ID NO 35
<211> LENGTH: 20
<212> TYPE: DNA
<213> ORGANISM: Staphylococcus aureus

<400> SEQUENCE: 35
agcaggatgg ttgaatgatg                                                    20
```

```
<210> SEQ ID NO 36
<211> LENGTH: 20
<212> TYPE: DNA
<213> ORGANISM: Staphylococcus aureus

<400> SEQUENCE: 36
tgtaaatgat attaagttac                                              20

<210> SEQ ID NO 37
<211> LENGTH: 22
<212> TYPE: DNA
<213> ORGANISM: Staphylococcus aureus

<400> SEQUENCE: 37
gaagatgacg ccttgataaa tc                                           22

<210> SEQ ID NO 38
<211> LENGTH: 21
<212> TYPE: DNA
<213> ORGANISM: Staphylococcus aureus

<400> SEQUENCE: 38
taatcgctgg taatagtgct t                                            21

<210> SEQ ID NO 39
<211> LENGTH: 23
<212> TYPE: DNA
<213> ORGANISM: Staphylococcus aureus

<400> SEQUENCE: 39
agtttgtcca aaagaattaa atc                                          23

<210> SEQ ID NO 40
<211> LENGTH: 18
<212> TYPE: DNA
<213> ORGANISM: Staphylococcus aureus

<400> SEQUENCE: 40
cattctgttc tcagcttc                                                18

<210> SEQ ID NO 41
<211> LENGTH: 678
<212> TYPE: DNA
<213> ORGANISM: Staphylococcus aureus
<220> FEATURE:
<221> NAME/KEY: CDS
<222> LOCATION: (1)...(678)
<221> NAME/KEY: misc_feature
<222> LOCATION: (1)...(678)
<223> OTHER INFORMATION: n = A,T,C or G

<400> SEQUENCE: 41 cac gag cga ttt att tca aca atc cgt agt ttt cat caa ttt gct ata    48
His Glu Arg Phe Ile Ser Thr Ile Arg Ser Phe His Gln Phe Ala Ile
 1               5                  10                  15 aga gaa aaa tat gcg gcg aaa gat cca acg gta tta tta gat tca cca    96
Arg Glu Lys Tyr Ala Ala Lys Asp Pro Thr Val Leu Leu Asp Ser Pro
             20                  25                  30 aaa tat gac aaa aaa ttg cct gac gtt tta aat gtt gac gaa gta ttg   144
Lys Tyr Asp Lys Lys Leu Pro Asp Val Leu Asn Val Asp Glu Val Leu
         35                  40                  45 gct tta tta gaa acg cca gat tta aat aaa att aat gga tat cgt gat   192
Ala Leu Leu Glu Thr Pro Asp Leu Asn Lys Ile Asn Gly Tyr Arg Asp
     50                  55                  60
```

```
cgt acg atg tta gaa ctt ctg tac gca acg gga atg cgt gta tct gaa    240
Arg Thr Met Leu Glu Leu Leu Tyr Ala Thr Gly Met Arg Val Ser Glu
 65                  70                  75                  80 ttg ata cat tta gag tta gaa aac gtg aac tta ata atg gga ttt gta    288
Leu Ile His Leu Glu Leu Glu Asn Val Asn Leu Ile Met Gly Phe Val
                 85                  90                  95 cgc gta ttt ggt aaa ggc gat aaa gaa aga att gta cca tta ggc gac    336
Arg Val Phe Gly Lys Gly Asp Lys Glu Arg Ile Val Pro Leu Gly Asp
            100                 105                 110 gca gtc att gag tac tta act act tat att gaa acg att aga ccg caa    384
Ala Val Ile Glu Tyr Leu Thr Thr Tyr Ile Glu Thr Ile Arg Pro Gln
        115                 120                 125 ctt tta aaa aag act gtt act gaa gtc tta ttt tta aat atg cat ggt    432
Leu Leu Lys Lys Thr Val Thr Glu Val Leu Phe Leu Asn Met His Gly
    130                 135                 140 aaa cct tta tca cga caa gca ata tgg aaa atg att aaa caa aat ggc    480
Lys Pro Leu Ser Arg Gln Ala Ile Trp Lys Met Ile Lys Gln Asn Gly
145                 150                 155                 160 gta aag gca aac att aaa aag aag tta acg cca cat acg tta cgc cac    528
Val Lys Ala Asn Ile Lys Lys Lys Leu Thr Pro His Thr Leu Arg His
                165                 170                 175 tct ttt gcg aca cat tta ttg gaa aat ggc gca gat tta aga gca gtg    576
Ser Phe Ala Thr His Leu Leu Glu Asn Gly Ala Asp Leu Arg Ala Val
            180                 185                 190 cna gaa atg tta ggt cac tct gac ata tct act acc caa ctc tat aca    624
Xaa Glu Met Leu Gly His Ser Asp Ile Ser Thr Thr Gln Leu Tyr Thr
        195                 200                 205 cat gtt tcg aaa tct caa att aaa aaa atg tat tac cca ttt cat cct    672
His Val Ser Lys Ser Gln Ile Lys Lys Met Tyr Tyr Pro Phe His Pro
    210                 215                 220 aaa aca                                                            678
Lys Thr
225

<210> SEQ ID NO 42
<211> LENGTH: 681
<212> TYPE: DNA
<213> ORGANISM: Staphylococcus aureus
<220> FEATURE:
<221> NAME/KEY: CDS
<222> LOCATION: (1)...(681)

<400> SEQUENCE: 42 agc tca gat tgg aga gat tgt atg aca ctt tca aaa gag aca gaa gtg     48
Ser Ser Asp Trp Arg Asp Cys Met Thr Leu Ser Lys Glu Thr Glu Val
  1               5                  10                  15 ata ttc gat tgg cgt aga ggt gtg gaa tat cat tca gct aac cca cca     96
Ile Phe Asp Trp Arg Arg Gly Val Glu Tyr His Ser Ala Asn Pro Pro
                 20                  25                  30 ctt tat gat ttt tca aca ttc cat caa aca agt ctt ggt ggc gat gtt    144
Leu Tyr Asp Phe Ser Thr Phe His Gln Thr Ser Leu Gly Gly Asp Val
            35                  40                  45 aaa tat gat tat gca cga agt ggc aac cct aac cgt gaa ctt tta gaa    192
Lys Tyr Asp Tyr Ala Arg Ser Gly Asn Pro Asn Arg Glu Leu Leu Glu
        50                  55                  60 gag aag tta gca cga tta gaa cag gga aaa ttc gct ttt gct ttt gca    240
Glu Lys Leu Ala Arg Leu Glu Gln Gly Lys Phe Ala Phe Ala Phe Ala
 65                  70                  75                  80 tca ggt att gct gct att tca gca gta ctt ttg act ttc aaa tct ggt    288
Ser Gly Ile Ala Ala Ile Ser Ala Val Leu Leu Thr Phe Lys Ser Gly
                 85                  90                  95
```

```
gat cat gtc atc tta ccc gat gat gta tat ggc ggt act ttt cgc ctc    336
Asp His Val Ile Leu Pro Asp Asp Val Tyr Gly Gly Thr Phe Arg Leu
        100                 105                 110 act gag caa att ttg aat cga ttt aat att gaa ttt aca acc gta gat    384
Thr Glu Gln Ile Leu Asn Arg Phe Asn Ile Glu Phe Thr Thr Val Asp
            115                 120                 125 act acc aag ctc gaa caa atc gag ggt gcc att caa tca aac aca aaa    432
Thr Thr Lys Leu Glu Gln Ile Glu Gly Ala Ile Gln Ser Asn Thr Lys
130                 135                 140 tta att tat atc gaa aca cca tcg aat ccc tgt ttt aaa att act gat    480
Leu Ile Tyr Ile Glu Thr Pro Ser Asn Pro Cys Phe Lys Ile Thr Asp
145                 150                 155                 160 atc aaa gct gtt tct aaa ata gcc gaa aag cat gaa cta ctg gta gct    528
Ile Lys Ala Val Ser Lys Ile Ala Glu Lys His Glu Leu Leu Val Ala
                165                 170                 175 gtg gac aat aca ttt atg aca ccg tta ggc caa tca cct tta tta ctt    576
Val Asp Asn Thr Phe Met Thr Pro Leu Gly Gln Ser Pro Leu Leu Leu
            180                 185                 190 ggc gct gat att gtc att cat agt gct acc aaa ttt tta agt gga cat    624
Gly Ala Asp Ile Val Ile His Ser Ala Thr Lys Phe Leu Ser Gly His
        195                 200                 205 agc gat tta att gct ggt gct gtc att act aat att gag cca att agt    672
Ser Asp Leu Ile Ala Gly Ala Val Ile Thr Asn Ile Glu Pro Ile Ser
    210                 215                 220 gaa gct ctt                                                        681
Glu Ala Leu
225

<210> SEQ ID NO 43
<211> LENGTH: 528
<212> TYPE: DNA
<213> ORGANISM: Staphylococcus aureus
<220> FEATURE:
<221> NAME/KEY: CDS
<222> LOCATION: (1)...(528)

<400> SEQUENCE: 43 cta gca tca gtt aat att gat ttt act gaa gct gcg aaa gaa att acg    48
Leu Ala Ser Val Asn Ile Asp Phe Thr Glu Ala Ala Lys Glu Ile Thr
1               5                   10                  15 gga gaa tta att gaa aaa ggc gct aaa tca ttt gct tta gta ggt gga    96
Gly Glu Leu Ile Glu Lys Gly Ala Lys Ser Phe Ala Leu Val Gly Gly
                20                  25                  30 gaa cat tct aaa aaa gct caa gaa gat gtt tta gaa ggt tta act gaa    144
Glu His Ser Lys Lys Ala Gln Glu Asp Val Leu Glu Gly Leu Thr Glu
            35                  40                  45 gtg tta aat aaa aat ggc ctt caa tta ggt gat aca ttg aat tgt tct    192
Val Leu Asn Lys Asn Gly Leu Gln Leu Gly Asp Thr Leu Asn Cys Ser
        50                  55                  60 ggt gct gaa agt tat aaa gaa ggc gta aaa gct ttt gct aaa atg aaa    240
Gly Ala Glu Ser Tyr Lys Glu Gly Val Lys Ala Phe Ala Lys Met Lys
65                  70                  75                  80 ggc aat ttg cca gat gcc att tta tgt atc agc gac gaa gaa gca att    288
Gly Asn Leu Pro Asp Ala Ile Leu Cys Ile Ser Asp Glu Glu Ala Ile
                85                  90                  95 ggt att atg cat agt gca atg gat gct ggt att aaa gtt cca gag gaa    336
Gly Ile Met His Ser Ala Met Asp Ala Gly Ile Lys Val Pro Glu Glu
            100                 105                 110 tta caa att att agt ttc aat aat aca cga tta gtt gag atg gtt aga    384
Leu Gln Ile Ile Ser Phe Asn Asn Thr Arg Leu Val Glu Met Val Arg
        115                 120                 125
```

```
cca caa ctt tct agt gtt att caa cca tta tat gat atc ggt gca gta      432
Pro Gln Leu Ser Ser Val Ile Gln Pro Leu Tyr Asp Ile Gly Ala Val
        130                 135                 140 ggg atg cgc tta tta aca aaa tat atg aac gat gaa aag ata caa gaa      480
Gly Met Arg Leu Leu Thr Lys Tyr Met Asn Asp Glu Lys Ile Gln Glu
145                 150                 155                 160 cca aat gta gtt tta cct cac aga att gaa tac cga gga act aca aaa      528
Pro Asn Val Val Leu Pro His Arg Ile Glu Tyr Arg Gly Thr Thr Lys
                165                 170                 175

<210> SEQ ID NO 44
<211> LENGTH: 663
<212> TYPE: DNA
<213> ORGANISM: Staphylococcus aureus
<220> FEATURE:
<221> NAME/KEY: CDS
<222> LOCATION: (1)...(663)
<221> NAME/KEY: misc_feature
<222> LOCATION: (1)...(663)
<223> OTHER INFORMATION: n = A,T,C or G

<400> SEQUENCE: 44 tgc agg aat tcg gca cga gcg gca cga gct ggt tcg cag gca aat caa       48
Cys Arg Asn Ser Ala Arg Ala Ala Arg Ala Gly Ser Gln Ala Asn Gln
1               5                   10                  15 tta cta caa caa gca aaa gcc caa att aat gca atg att aat tca aaa       96
Leu Leu Gln Gln Ala Lys Ala Gln Ile Asn Ala Met Ile Asn Ser Lys
            20                  25                  30 aca aat tat gat gtt gta ttc act agt ggt gca act gaa tcc aat aat      144
Thr Asn Tyr Asp Val Val Phe Thr Ser Gly Ala Thr Glu Ser Asn Asn
        35                  40                  45 ctt gct tta aaa ggt att gcc tat cgt aaa ttt gat aca gcg aag gaa      192
Leu Ala Leu Lys Gly Ile Ala Tyr Arg Lys Phe Asp Thr Ala Lys Glu
    50                  55                  60 ata att aca tcc gtg tta gag cat ccg tcc gta tta gag gtt gta aga      240
Ile Ile Thr Ser Val Leu Glu His Pro Ser Val Leu Glu Val Val Arg
65                  70                  75                  80 tat ttg gaa gca cac gaa gga ttt aaa gtt aaa tat gtt gat gta aag      288
Tyr Leu Glu Ala His Glu Gly Phe Lys Val Lys Tyr Val Asp Val Lys
                85                  90                  95 aaa gat ggc agt att aac tta gaa cac ttc aaa gaa tta gtg tca gac      336
Lys Asp Gly Ser Ile Asn Leu Glu His Phe Lys Glu Leu Val Ser Asp
            100                 105                 110 aaa gtc ggt tta gta aca tgt atg tat gta aat aat gta act gga caa      384
Lys Val Gly Leu Val Thr Cys Met Tyr Val Asn Asn Val Thr Gly Gln
        115                 120                 125 ata cag cct att cca caa atg gct aaa gtt ata aaa aat tat cct aag      432
Ile Gln Pro Ile Pro Gln Met Ala Lys Val Ile Lys Asn Tyr Pro Lys
    130                 135                 140 gca cat ttt cat gta gat gcg gct caa gca ttc ggc aaa att tca atg      480
Ala His Phe His Val Asp Ala Ala Gln Ala Phe Gly Lys Ile Ser Met
145                 150                 155                 160 gat ctc aat aac ata gat agt att agt tta agt gga cac aag ttt ant      528
Asp Leu Asn Asn Ile Asp Ser Ile Ser Leu Ser Gly His Lys Phe Xaa
                165                 170                 175 ggt tta aaa gga caa ggc gtc tta ctt gta aat cac ata caa aat gtt      576
Gly Leu Lys Gly Gln Gly Val Leu Leu Val Asn His Ile Gln Asn Val
            180                 185                 190 gga cca tct gtc cat ggt ggt ggt caa gaa tat ggc gtt aga agt gga      624
Gly Pro Ser Val His Gly Gly Gly Gln Glu Tyr Gly Val Arg Ser Gly
        195                 200                 205
```

```
aca gtt aat tgc caa atg ata ttg caa tgg tta aag cga                    663
Thr Val Asn Cys Gln Met Ile Leu Gln Trp Leu Lys Arg
    210                 215                 220

<210> SEQ ID NO 45
<211> LENGTH: 348
<212> TYPE: DNA
<213> ORGANISM: Staphylococcus aureus
<220> FEATURE:
<221> NAME/KEY: CDS
<222> LOCATION: (1)...(348)

<400> SEQUENCE: 45 ttt gta gca gga tgg ttg aat gat gct cta cat acc gaa atg att gtt         48
Phe Val Ala Gly Trp Leu Asn Asp Ala Leu His Thr Glu Met Ile Val
1               5                   10                  15 gat ggc aca cat tct cat ccg gca tcg gtt gca att gct tac cgt atg         96
Asp Gly Thr His Ser His Pro Ala Ser Val Ala Ile Ala Tyr Arg Met
            20                  25                  30 aaa ggt aat gaa cgt ttt tat tta att acc gat gca atg cgt gca aaa        144
Lys Gly Asn Glu Arg Phe Tyr Leu Ile Thr Asp Ala Met Arg Ala Lys
        35                  40                  45 ggt atg cct gaa gga gaa tat gat ttg ggt gga caa aaa gta act gtt        192
Gly Met Pro Glu Gly Glu Tyr Asp Leu Gly Gly Gln Lys Val Thr Val
50                  55                  60 caa tcg caa caa gca cgt ctt gca aat ggt gcg ctt gct ggt agt att        240
Gln Ser Gln Gln Ala Arg Leu Ala Asn Gly Ala Leu Ala Gly Ser Ile
65                  70                  75                  80 tta aaa atg aat cat ggg tta cgt aac tta ata tca ttt aca ggt gat        288
Leu Lys Met Asn His Gly Leu Arg Asn Leu Ile Ser Phe Thr Gly Asp
                85                  90                  95 aca tta gat cat tta tgg cga gta aca agt tta aat caa gcc att gca        336
Thr Leu Asp His Leu Trp Arg Val Thr Ser Leu Asn Gln Ala Ile Ala
            100                 105                 110 tta ggt atc gca                                                        348
Leu Gly Ile Ala
        115

<210> SEQ ID NO 46
<211> LENGTH: 933
<212> TYPE: DNA
<213> ORGANISM: Staphylococcus aureus
<220> FEATURE:
<221> NAME/KEY: CDS
<222> LOCATION: (1)...(933)

<400> SEQUENCE: 46 tta tta aca ctc tcc gag gat tta aaa cgt gct aaa tat att ggc act         48
Leu Leu Thr Leu Ser Glu Asp Leu Lys Arg Ala Lys Tyr Ile Gly Thr
1               5                   10                  15 gaa aag cct atg tta aaa aat aaa aat att gca ctg tta ttt gaa aaa         96
Glu Lys Pro Met Leu Lys Asn Lys Asn Ile Ala Leu Leu Phe Glu Lys
            20                  25                  30 gat tct aca aga acg cga tgt gca ttt gaa gtt gca gcg cat gat caa        144
Asp Ser Thr Arg Thr Arg Cys Ala Phe Glu Val Ala Ala His Asp Gln
        35                  40                  45 ggt gca aat gta act tat tta ggc cca act gga tca caa atg ggt aaa        192
Gly Ala Asn Val Thr Tyr Leu Gly Pro Thr Gly Ser Gln Met Gly Lys
50                  55                  60 aaa gaa aca act aaa gat act gca cgt gtg ctt ggt gga atg tat gat        240
Lys Glu Thr Thr Lys Asp Thr Ala Arg Val Leu Gly Gly Met Tyr Asp
65                  70                  75                  80 ggc att gaa tac cgg agt ttt tca caa aga aca gta gaa act tta gct        288
```

```
Gly Ile Glu Tyr Arg Ser Phe Ser Gln Arg Thr Val Glu Thr Leu Ala
                85                  90                  95 gaa tat tca ggc gta cca gtg tgg aat ggt tta act gat gaa gat cat      336
Glu Tyr Ser Gly Val Pro Val Trp Asn Gly Leu Thr Asp Glu Asp His
            100                 105                 110 cct act caa gtt ctt gct gat ttc tta aca gca aaa gaa gtc tta aaa      384
Pro Thr Gln Val Leu Ala Asp Phe Leu Thr Ala Lys Glu Val Leu Lys
        115                 120                 125 aaa gat tat gca gat att aac ttt aca tat gtt gga gat ggt cgt aat      432
Lys Asp Tyr Ala Asp Ile Asn Phe Thr Tyr Val Gly Asp Gly Arg Asn
    130                 135                 140 aac gtt gca aat gca tta atg caa ggt gct gcc att atg ggt atg aac      480
Asn Val Ala Asn Ala Leu Met Gln Gly Ala Ala Ile Met Gly Met Asn
145                 150                 155                 160 ttc cat tta gtt tgt cca aaa gaa tta aat cca aca gat gaa tta tta      528
Phe His Leu Val Cys Pro Lys Glu Leu Asn Pro Thr Asp Glu Leu Leu
                165                 170                 175 aat cgc tgt aaa aat att gcc gct gaa aat ggt ggc aac ata tta atc      576
Asn Arg Cys Lys Asn Ile Ala Ala Glu Asn Gly Gly Asn Ile Leu Ile
            180                 185                 190 aca gat gat att gac caa ggt gta aaa ggt tcg gat gta att tac act      624
Thr Asp Asp Ile Asp Gln Gly Val Lys Gly Ser Asp Val Ile Tyr Thr
        195                 200                 205 gat gtt tgg gta tca atg ggt gaa cct gat gaa gta tgg aaa gaa cga      672
Asp Val Trp Val Ser Met Gly Glu Pro Asp Glu Val Trp Lys Glu Arg
    210                 215                 220 ctt gaa tta ttg aaa cca tat caa gta aat aaa gaa atg atg gat aaa      720
Leu Glu Leu Leu Lys Pro Tyr Gln Val Asn Lys Glu Met Met Asp Lys
225                 230                 235                 240 act ggt aat cca aat gtt att ttt gag cat tgc tta cca tct ttc cat      768
Thr Gly Asn Pro Asn Val Ile Phe Glu His Cys Leu Pro Ser Phe His
                245                 250                 255 aat gct gat acg aaa att ggt caa caa att ttt gaa aaa tat ggt att      816
Asn Ala Asp Thr Lys Ile Gly Gln Gln Ile Phe Glu Lys Tyr Gly Ile
            260                 265                 270 cga gaa atg gaa gtt aca gat gaa gta ttc gaa agt aaa gct tca gtt      864
Arg Glu Met Glu Val Thr Asp Glu Val Phe Glu Ser Lys Ala Ser Val
        275                 280                 285 gta ttc caa gaa gct gag aac aga atg cat aca atc aaa gca gtc atg      912
Val Phe Gln Glu Ala Glu Asn Arg Met His Thr Ile Lys Ala Val Met
    290                 295                 300 gtt gct aca ttg ggt gaa ttt                                          933
Val Ala Thr Leu Gly Glu Phe
305                 310

<210> SEQ ID NO 47
<211> LENGTH: 226
<212> TYPE: PRT
<213> ORGANISM: Staphylococcus aureus
<220> FEATURE:
<221> NAME/KEY: VARIANT
<222> LOCATION: (1)...(226)
<223> OTHER INFORMATION: Xaa = Any Amino Acid

<400> SEQUENCE: 47

His Glu Arg Phe Ile Ser Thr Ile Arg Ser Phe His Gln Phe Ala Ile
 1               5                  10                  15

Arg Glu Lys Tyr Ala Ala Lys Asp Pro Thr Val Leu Leu Asp Ser Pro
            20                  25                  30

Lys Tyr Asp Lys Lys Leu Pro Asp Val Leu Asn Val Asp Glu Val Leu
        35                  40                  45
```

```
Ala Leu Leu Glu Thr Pro Asp Leu Asn Lys Ile Asn Gly Tyr Arg Asp
     50                  55                  60

Arg Thr Met Leu Glu Leu Tyr Ala Thr Gly Met Arg Val Ser Glu
 65                  70                  75                  80

Leu Ile His Leu Glu Leu Glu Asn Val Asn Leu Ile Met Gly Phe Val
                 85                  90                  95

Arg Val Phe Gly Lys Gly Asp Lys Glu Arg Ile Val Pro Leu Gly Asp
             100                 105                 110

Ala Val Ile Glu Tyr Leu Thr Thr Tyr Ile Glu Thr Ile Arg Pro Gln
         115                 120                 125

Leu Leu Lys Lys Thr Val Thr Glu Val Leu Phe Leu Asn Met His Gly
     130                 135                 140

Lys Pro Leu Ser Arg Gln Ala Ile Trp Lys Met Ile Lys Gln Asn Gly
145                 150                 155                 160

Val Lys Ala Asn Ile Lys Lys Leu Thr Pro His Thr Leu Arg His
                 165                 170                 175

Ser Phe Ala Thr His Leu Leu Glu Asn Gly Ala Asp Leu Arg Ala Val
             180                 185                 190

Xaa Glu Met Leu Gly His Ser Asp Ile Ser Thr Thr Gln Leu Tyr Thr
         195                 200                 205

His Val Ser Lys Ser Gln Ile Lys Lys Met Tyr Tyr Pro Phe His Pro
     210                 215                 220

Lys Thr
225

<210> SEQ ID NO 48
<211> LENGTH: 227
<212> TYPE: PRT
<213> ORGANISM: Staphylococcus aureus

<400> SEQUENCE: 48

Ser Ser Asp Trp Arg Asp Cys Met Thr Leu Ser Lys Glu Thr Glu Val
  1               5                  10                  15

Ile Phe Asp Trp Arg Arg Gly Val Glu Tyr His Ser Ala Asn Pro Pro
                 20                  25                  30

Leu Tyr Asp Phe Ser Thr Phe His Gln Thr Ser Leu Gly Gly Asp Val
             35                  40                  45

Lys Tyr Asp Tyr Ala Arg Ser Gly Asn Pro Asn Arg Glu Leu Leu Glu
     50                  55                  60

Glu Lys Leu Ala Arg Leu Glu Gln Gly Lys Phe Ala Phe Ala Phe Ala
 65                  70                  75                  80

Ser Gly Ile Ala Ala Ile Ser Ala Val Leu Leu Thr Phe Lys Ser Gly
                 85                  90                  95

Asp His Val Ile Leu Pro Asp Ala Val Tyr Gly Gly Thr Phe Arg Leu
             100                 105                 110

Thr Glu Gln Ile Leu Asn Arg Phe Asn Ile Glu Phe Thr Thr Val Asp
         115                 120                 125

Thr Thr Lys Leu Glu Gln Ile Glu Gly Ala Ile Gln Ser Asn Thr Lys
     130                 135                 140

Leu Ile Tyr Ile Glu Thr Pro Ser Asn Pro Cys Phe Lys Ile Thr Asp
145                 150                 155                 160

Ile Lys Ala Val Ser Lys Ile Ala Glu Lys His Glu Leu Leu Val Ala
                 165                 170                 175

Val Asp Asn Thr Phe Met Thr Pro Leu Gly Gln Ser Pro Leu Leu Leu
```

```
                      180                 185                 190
Gly Ala Asp Ile Val Ile His Ser Ala Thr Lys Phe Leu Ser Gly His
        195                 200                 205

Ser Asp Leu Ile Ala Gly Ala Val Ile Thr Asn Ile Glu Pro Ile Ser
    210                 215                 220

Glu Ala Leu
225

<210> SEQ ID NO 49
<211> LENGTH: 176
<212> TYPE: PRT
<213> ORGANISM: Staphylococcus aureus

<400> SEQUENCE: 49

Leu Ala Ser Val Asn Ile Asp Phe Thr Glu Ala Ala Lys Glu Ile Thr
1               5                   10                  15

Gly Glu Leu Ile Glu Lys Gly Ala Lys Ser Phe Ala Leu Val Gly Gly
            20                  25                  30

Glu His Ser Lys Lys Ala Gln Glu Asp Val Leu Glu Gly Leu Thr Glu
        35                  40                  45

Val Leu Asn Lys Asn Gly Leu Gln Leu Gly Asp Thr Leu Asn Cys Ser
    50                  55                  60

Gly Ala Glu Ser Tyr Lys Gly Val Lys Ala Phe Ala Lys Met Lys
65                  70                  75                  80

Gly Asn Leu Pro Asp Ala Ile Leu Cys Ile Ser Asp Glu Glu Ala Ile
                85                  90                  95

Gly Ile Met His Ser Ala Met Asp Ala Gly Ile Lys Val Pro Glu Glu
            100                 105                 110

Leu Gln Ile Ile Ser Phe Asn Asn Thr Arg Leu Val Glu Met Val Arg
        115                 120                 125

Pro Gln Leu Ser Ser Val Ile Gln Pro Leu Tyr Asp Ile Gly Ala Val
    130                 135                 140

Gly Met Arg Leu Leu Thr Lys Tyr Met Asn Asp Glu Lys Ile Gln Glu
145                 150                 155                 160

Pro Asn Val Val Leu Pro His Arg Ile Glu Tyr Arg Gly Thr Thr Lys
                165                 170                 175

<210> SEQ ID NO 50
<211> LENGTH: 221
<212> TYPE: PRT
<213> ORGANISM: Staphylococcus aureus

<400> SEQUENCE: 50

Cys Arg Asn Ser Ala Arg Ala Ala Arg Ala Gly Ser Gln Ala Asn Gln
1               5                   10                  15

Leu Leu Gln Gln Ala Lys Ala Gln Ile Asn Ala Met Ile Asn Ser Lys
            20                  25                  30

Thr Asn Tyr Asp Val Val Phe Thr Ser Gly Ala Thr Glu Ser Asn Asn
        35                  40                  45

Leu Ala Leu Lys Gly Ile Ala Tyr Arg Lys Phe Asp Thr Ala Lys Glu
    50                  55                  60

Ile Ile Thr Ser Val Leu Glu His Pro Ser Val Leu Glu Val Val Arg
65                  70                  75                  80

Tyr Leu Glu Ala His Glu Gly Phe Lys Val Lys Tyr Val Asp Val Lys
                85                  90                  95

Lys Asp Gly Ser Ile Asn Leu Glu His Phe Lys Glu Leu Val Ser Asp
```

```
            100                 105                 110
Lys Val Gly Leu Val Thr Cys Met Tyr Val Asn Asn Val Thr Gly Gln
            115                 120                 125

Ile Gln Pro Ile Pro Gln Met Ala Lys Val Ile Lys Asn Tyr Pro Lys
        130                 135                 140

Ala His Phe His Val Asp Ala Ala Gln Ala Phe Gly Lys Ile Ser Met
145                 150                 155                 160

Asp Leu Asn Asn Ile Asp Ser Ile Ser Leu Ser Gly His Lys Phe Xaa
                165                 170                 175

Gly Leu Lys Gly Gln Gly Val Leu Leu Val Asn His Ile Gln Asn Val
            180                 185                 190

Gly Pro Ser Val His Gly Gly Gln Glu Tyr Gly Val Arg Ser Gly
            195                 200                 205

Thr Val Asn Cys Gln Met Ile Leu Gln Trp Leu Lys Arg
        210                 215                 220
```

<210> SEQ ID NO 51
<211> LENGTH: 116
<212> TYPE: PRT
<213> ORGANISM: Staphylococcus aureus

<400> SEQUENCE: 51

```
Phe Val Ala Gly Trp Leu Asn Asp Ala Leu His Thr Glu Met Ile Val
1               5                   10                  15

Asp Gly Thr His Ser His Pro Ala Ser Val Ala Ile Ala Tyr Arg Met
            20                  25                  30

Lys Gly Asn Glu Arg Phe Tyr Leu Ile Thr Asp Ala Met Arg Ala Lys
        35                  40                  45

Gly Met Pro Glu Gly Glu Tyr Asp Leu Gly Gly Gln Lys Val Thr Val
    50                  55                  60

Gln Ser Gln Gln Ala Arg Leu Ala Asn Gly Ala Leu Ala Gly Ser Ile
65                  70                  75                  80

Leu Lys Met Asn His Gly Leu Arg Asn Leu Ile Ser Phe Thr Gly Asp
                85                  90                  95

Thr Leu Asp His Leu Trp Arg Val Thr Ser Leu Asn Gln Ala Ile Ala
            100                 105                 110

Leu Gly Ile Ala
        115
```

<210> SEQ ID NO 52
<211> LENGTH: 311
<212> TYPE: PRT
<213> ORGANISM: Staphylococcus aureus

<400> SEQUENCE: 52

```
Leu Leu Thr Leu Ser Glu Asp Leu Lys Arg Ala Lys Tyr Ile Gly Thr
1               5                   10                  15

Glu Lys Pro Met Leu Lys Asn Lys Asn Ile Ala Leu Leu Phe Glu Lys
            20                  25                  30

Asp Ser Thr Arg Thr Arg Cys Ala Phe Glu Val Ala Ala His Asp Gln
        35                  40                  45

Gly Ala Asn Val Thr Tyr Leu Gly Pro Thr Gly Ser Gln Met Gly Lys
    50                  55                  60

Lys Glu Thr Thr Lys Asp Thr Ala Arg Val Leu Gly Gly Met Tyr Asp
65                  70                  75                  80

Gly Ile Glu Tyr Arg Ser Phe Ser Gln Arg Thr Val Glu Thr Leu Ala
```

-continued

```
                     85                  90                    95
Glu Tyr Ser Gly Val Pro Val Trp Asn Gly Leu Thr Asp Glu Asp His
            100                 105                 110

Pro Thr Gln Val Leu Ala Asp Phe Leu Thr Ala Lys Glu Val Leu Lys
            115                 120                 125

Lys Asp Tyr Ala Asp Ile Asn Phe Thr Tyr Val Gly Asp Gly Arg Asn
            130                 135                 140

Asn Val Ala Asn Ala Leu Met Gln Gly Ala Ala Ile Met Gly Met Asn
145                 150                 155                 160

Phe His Leu Val Cys Pro Lys Glu Leu Asn Pro Thr Asp Glu Leu Leu
                165                 170                 175

Asn Arg Cys Lys Asn Ile Ala Ala Glu Asn Gly Gly Asn Ile Leu Ile
                180                 185                 190

Thr Asp Asp Ile Asp Gln Gly Val Lys Gly Ser Asp Val Ile Tyr Thr
            195                 200                 205

Asp Val Trp Val Ser Met Gly Glu Pro Asp Glu Val Trp Lys Glu Arg
    210                 215                 220

Leu Glu Leu Leu Lys Pro Tyr Gln Val Asn Lys Glu Met Met Asp Lys
225                 230                 235                 240

Thr Gly Asn Pro Asn Val Ile Phe Glu His Cys Leu Pro Ser Phe His
                245                 250                 255

Asn Ala Asp Thr Lys Ile Gly Gln Gln Ile Phe Glu Lys Tyr Gly Ile
                260                 265                 270

Arg Glu Met Glu Val Thr Asp Glu Val Phe Glu Ser Lys Ala Ser Val
            275                 280                 285

Val Phe Gln Glu Ala Glu Asn Arg Met His Thr Ile Lys Ala Val Met
    290                 295                 300

Val Ala Thr Leu Gly Glu Phe
305                 310
```

PROKARYOTIC POLYNUCLEOTIDES, POLYPEPTIDES AND THEIR USES

RELATED APPLICATIONS

This application claims benefit to U.S. Provisional Patent Application Ser. No. 60/058,710 filed Sep. 12, 1997.

FIELD OF THE INVENTION

This invention relates to newly identified polynucleotides and polypeptides, and their production and uses, as well as their variants, agonists and antagonists, and their uses. In particular, in these and in other regards, the invention relates to novel polynucleotides and polypeptides set forth in the Sequence Listing.

BACKGROUND OF THE INVENTION

It is particularly preferred to employ Staphylococcal genes and gene products as targets for the development of antibiotics. The Staphylococci make up a medically important genera of microbes. They are known to produce two types of disease, invasive and toxigenic. Invasive infections are characterized generally by abscess formation effecting both skin surfaces and deep tissues. *Staphylococcus aureus* is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome.

The frequency of *Staphylococcus aureus* infections has risen dramatically in the past 20 years. This has been attributed to the emergence of multiply antibiotic resistant strains and an increasing population of people with weakened immune systems. It is no longer uncommon to isolate *Staphylococcus aureus* strains which are resistant to some or all of the standard antibiotics. This has created a demand for both new anti-microbial agents and diagnostic tests for this organism.

Substantial effort has been invested this century in the successful discovery and development of antibacterials. Paradoxically, although antibacterials are devised to eradicate infection in mammals, we know almost nothing of the physiology of bacterial pathogens in infective situations in the host. Using sequences from the *Staphylococcus aureus* chromosome, we have developed an RT-PCR based procedure which allows us to identify those bacterial genes transcribed at any stage of infection and also from different niches of infection. The derivation of such information is a critical first step in understanding the global response of the bacterial gene complement to the host environment. From the knowledge of bacterial genes both of known and unknown function which are widely transcribed in the host it is possible to attempt to ascertain by database searching those which are present only in the eubacteria. Further prioritization of such genes by consideration of the likely role of their products towards the maintenance of infection and the facility of setting up a screen for inhibitors of the biochemical function indicated by their homology to characterised genes allows the compilation of a shortlist for gene essentiality studies using genetic deletion or controlled regulation techniques. The proteins expressed by genes shown to be necessary for growth in vitro or in pathogenesis in animal models provide novel targets for antibacterial screening to find agents which are broadly inhibitory towards pathogenesis. This invention provides *Staphylococcus aureus* WCUH 29 polynucleotides which are transcribed in infected tissue, in particular in both acute and chronic infections.

Clearly, there is a need for factors, such as the novel compounds of the invention, that have a present benefit of being useful to screen compounds for antibiotic activity. Such factors are also useful to determine their role in pathogenesis of infection, dysfunction and disease. There is also a need for identification and characterization of such factors and their antagonists and agonists which can play a role in preventing, ameliorating or correcting infections, dysfunctions or diseases.

The polypeptides of the invention have amino acid sequence homology to a known protein(s) as set forth in Table 1.

SUMMARY OF THE INVENTION

It is an object of the invention to provide polypeptides that have been identified as novel polypeptides by homology between an amino acid sequence selected from the group consisting of the sequences set out in the Sequence Listing and a known amino acid sequence or sequences of other proteins such as the protein identities listed in Table 1.

It is a further object of the invention to provide polynucleotides that encode novel polypeptides, particularly polynucleotides that encode polypeptides of *Staphylococcus aureus*.

In a particularly preferred embodiment of the invention, the polynucleotide comprises a region encoding a polypeptide comprising a sequence sequence selected from the group consisting of the sequences set out in the Sequence Listing, or a variant of any of these sequences.

In another particularly preferred embodiment of the invention, there is a novel protein from *Staphylococcus aureus* comprising an amino acid sequence selected from the group consisting of the sequences set out in the Sequence Listing, or a variant of any of these sequences.

In accordance with another aspect of the invention, there is provided an isolated nucleic acid molecule encoding a mature polypeptide expressible by the *Staphylococcus aureus* WCUH 29 strain contained in the deposited strain.

As a further aspect of the invention, there are provided isolated nucleic acid molecules encoding a polypeptide of the invention, particularly *Staphylococcus aureus* polypeptide, and including mRNAs, cDNAs, genomic DNAs. Further embodiments of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of the invention are naturally occurring allelic variants of a polypeptide of the invention and polypeptides encoded thereby.

As another aspect of the invention, there are provided novel polypeptides of *Staphylococcus aureus* as well as biologically, diagnostically, prophylactically, clinically or therapeutically useful variants thereof, and compositions comprising the same.

Among the particularly preferred embodiments of the invention are variants of the polypeptides of the invention encoded by naturally occurring alleles of their genes.

In a preferred embodiment of the invention, there are provided methods for producing the aforementioned polypeptides.

In accordance with yet another aspect of the invention, there are provided inhibitors to such polypeptides, useful as antibacterial agents, including, for example, antibodies.

In accordance with certain preferred embodiments of the invention, there are provided products, compositions and methods for assessing expression of the polypeptides and polynucleotides of the invention, treating disease, for example, disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric abscess, toxic shock syndrome), skin (e.g., impetigo, folliculitis, cutaneous abscesses, cellulitis, wound infection, bacterial myositis) bone and joint (e.g., septic arthritis, osteomyelitis), assaying genetic variation, and administering a polypeptide or polynucleotide of the invention to an organism to raise an immunological response against a bacteria, especially a *Staphylococcus aureus* bacteria.

In accordance with certain preferred embodiments of this and other aspects of the invention, there are provided polynucleotides that hybridize to a polynucleotide sequence of the invention, particularly under stringent conditions.

In certain preferred embodiments of the invention, there are provided antibodies against polypeptides of the invention.

In other embodiments of the invention, there are provided methods for identifying compounds which bind to or otherwise interact with and inhibit or activate an activity of a polypeptide or polynucleotide of the invention comprising: contacting a polypeptide or polynucleotide of the invention with a compound to be screened under conditions to permit binding to or other interaction between the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypeptide or polynucleotide by detecting the presence or absence of a signal generated from the binding or interaction of the compound with the polypeptide or polynucleotide.

In accordance with yet another aspect of the invention, there are provided agonists and antagonists of the polypeptides and polynucleotides of the invention, preferably bacteriostatic or bacteriocidal agonists and antagonists.

In a further aspect of the invention, there are provided compositions comprising a polynucleotide or a polypeptide of the invention for administration to a cell or to a multicellular organism.

Various changes and modifications within the spirit and scope of the disclosed invention will become readily apparent to those skilled in the art from reading the following descriptions and from reading the other parts of the present disclosure.

GLOSSARY

The following definitions are provided to facilitate understanding of certain terms used frequently herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following: Algorithm:
Needleman and Wunsch, J. Mol Biol. 48: 443–453 (1970)
Comparison matrix: BLOSSUM62 from Hentikoff and Hentikoff, Proc. Natl. Acad. Sci. USA. 89:10915–10919 (1992)
Gap Penalty: 12
Gap Length Penalty: 4
A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following: Algorithm:
Needleman and Wunsch, J. Mol Biol. 48: 443–453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:1, that is it may be 100% identical, or it may include up to a certain integer number of nucleic acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leq x_n - (x_n \cdot y),$$

wherein $n_n$ is the number of nucleic acid alterations, $x_n$ is the total number of nucleic acids in SEQ ID NO:1, y is, for instance 0.70 for 70%, 0.80 for 80%, 0.85 for 85% etc., · is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50,60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES,* 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS,* B. C. Johnson, Ed., Academic Press, New York (1983); Seifter et al., *Meth. Enzymol.* 182:626–646 (1990) and Rattan et al., *Protein Synthesis: Posttranslational Modifications and Aging,* Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DESCRIPTION OF THE INVENTION

Each of polynucleotide and polypeptide sequences provided herein may be used in the discovery and development of antibacterial compounds. Upon expression of the sequences with the appropriate initiation and termination codons the encoded polypeptide can be used as a target for the screening of antimicrobial drugs. Additionally, the DNA sequences encoding preferably the amino terminal regions of the encoded protein or the Shine-Delgarno region can be used to construct antisense sequences to control the expression of the coding sequence of interest. Furthermore, many of the sequences disclosed herein also provide regions upstream and downstream from the encoding sequence. These sequences are useful as a source of regulatory elements for the control of bacterial gene expression. Such sequences are conveniently isolated by restriction enzyme action or synthesized chemically and introduced, for example, into promoter identification strains. These strains contain a reporter structural gene sequence located downstream from a restriction site such that, if an active promoter is inserted, the reporter gene will be expressed.

Although each of the sequences may be employed as described above, this invention also provides several means for identifying particularly useful target genes. The first of these approaches entails searching appropriate databases for sequence matches in related organisms. Thus, if a homologue exists, the Staphyococcal-like form of this gene would likely play an analogous role. For example, a Staphyococcal protein identified as homologous to a cell surface protein in another organism would be useful as a vaccine candidate. To the extent such homologies have been identified for the sequences disclosed herein they are reported along with the encoding sequence.

ORF Gene Expression

Recently, techniques have become available to evaluate temporal gene expression in bacteria, particularly as it applies to viability under laboratory and infection conditions. A number of methods can be used to identify genes which are essential to survival per se, or essential to the establishment/maintenance of an infection. Identification of an ORF unknown by one of these methods yields additional information about its function and permits the selection of such an ORF for further development as a screening target. Briefly, these approaches include:

1) Signature Tagged Mutagenesis (STM): This technique is described by Hensel et al., *Science* 269: 400–403 (1995), the contents of which is incorporated by reference for background purposes. Signature tagged mutagenesis identifies genes necessary for the establishment/maintenance of infection in a given infection model.

The basis of the technique is the random mutagenesis of target organism by various means (e.g., transposons) such that unique DNA sequence tags are inserted in close proximity to the site of mutation. The tags from a mixed population of bacterial mutants and bacteria recovered from an infected hosts are detected by amplification, radiolabeling and hybridization analysis. Mutants attenuated in virulence are revealed by absence of the tag from the pool of bacteria recovered from infected hosts.

In *Staphylococcus aureus*, because the transposon system is less well developed, a more efficient way of creating the tagged mutants is to use the insertion-duplication mutagenesis technique as described by Morrison et al., *J. Bacteriol.* 159:870 (1984) the contents of which is incorporated by reference for background purposes.

2) In Vivo Expression Technology (IVET): This technique is described by Camilli et al., *Proc. Nat'l. Acad. Sci. USA.* 91:2634–2638 (1994), the contents of which is incorporated by reference for background purposes. IVET identifies genes up-regulated during infection when compared to laboratory cultivation, implying an important role in infection. ORF identified by this technique are implied to have a significant role in infection establishment/maintenance.

In this technique random chromosomal fragments of target organism are cloned upstream of a promoter-less recombinase gene in a plasmid vector. This construct is introduced into the target organism which carries an antibiotic resistance gene flanked by resolvase sites. Growth in the presence of the antibiotic removes from the population those fragments cloned into the plasmid vector capable of supporting transcription of the recombinase gene and therefore have caused loss of antibiotic resistance. The resistant pool is introduced into a host and at various times after infection bacteria may be recovered and assessed for the presence of antibiotic resistance. The chromosomal fragment carried by each antibiotic sensitive bacterium should carry a promoter or portion of a gene normally upregulated during infection. Sequencing upstream of the recombinase gene allows identification of the up regulated gene.

3) Differential display: This technique is described by Chuang et al., *J. Bacteriol.* 175:2026–2036 (1993), the contents of which is incorporated by reference for background purposes. This method identifies those genes which are expressed in an organism by identifying mRNA present using randomly-primed RT-PCR. By comparing pre-infection and post infection profiles, genes up and down regulated during infection can be identified and the RT-PCR product sequenced and matched to ORF 'unknowns'.

4) Generation of conditional lethal mutants by transposon mutagenesis: This technique, described by de Lorenzo, V. et al., *Gene,* 123:17–24 (1993); Neuwald, A. F. et al., *Gene,* 125: 69–73 (1993); and Takiff, H. E. et al., *J. Bacteriol.,* 174:1544–1553 (1992), the contents of which are incorporated by reference for background purposes, identifies genes whose expression are essential for cell viability.

In this technique, transposons carrying controllable promoters, which provide transcription outward from the transposon in one or both directions, are generated. Random insertion of these transposons into target organisms and subsequent isolation of insertion mutants in the presence of inducer of promoter activity ensures that insertions which separate promoter from coding region of a gene whose expression is essential for cell viability will be recovered. Subsequent replica plating in the absence of inducer identifies such insertions, since they fail to survive. Sequencing of the flanking regions of the transposon allows identification of site of insertion and identification of the gene disrupted. Close monitoring of the changes in cellular processes/morphology during growth in the absence of inducer yields information on likely function of the gene. Such monitoring could include flow cytometry (cell division, lysis, redox potential, DNA replication), incorporation of radiochemically labeled precursors into DNA, RNA, protein, lipid, peptidoglycan, monitoring reporter enzyme gene fusions which respond to known cellular stresses.

5) Generation of conditional lethal mutants by chemical mutagenesis: This technique is described by Beckwith, *J. Methods in Enzymology,* 204: 3–18 (1991), the contents of which is incorporated herein by reference for background purposes. In this technique random chemical mutagenesis of target organism, growth at temperature other than physiological temperature (permissive temperature) and subsequent replica plating and growth at different temperature (e.g. 42° C. to identify ts, 25° C. to identify cs) are used to identify those isolates which now fail to grow (conditional mutants). As above close monitoring of the changes upon growth at the non-permissive temperature yields information on the function of the mutated gene. Complementation of conditional lethal mutation by library from target organism and sequencing of complementing gene allows matching with unknown ORF.

6) RT-PCR: *Staphylococcus aureus* messenger RNA is isolated from bacterial infected tissue e.g. 48 hour murine lung infections, and the amount of each mRNA species assessed by reverse transcription of the RNA sample primed with random hexanucleotides followed by PCR with gene specific primer pairs. The determination of the presence and amount of a particular mRNA species by quantification of the resultant PCR product provides information on the bacterial genes which are transcribed in the infected tissue. Analysis of gene transcription can be carried out at different times of infection to gain a detailed knowledge of gene regulation in bacterial pathogenesis allowing for a clearer understanding of which gene products represent targets for screens for novel antibacterials. Because of the gene specific nature of the PCR primers employed it should be understood that the bacterial mRNA preparation need not be free of mammalian RNA. This allows the investigator to carry out a simple and quick RNA preparation from infected tissue to obtain bacterial mRNA species which are very short lived in the bacterium (in the order of 2 minute halflives). Optimally the bacterial mRNA is prepared from infected murine lung tissue by mechanical disruption in the presence of TRIzole (GIBCO-BRL) for very short periods of time, subsequent processing according to the manufacturers of TRIzole reagent and DNAase treatment to remove contaminating DNA. Preferably the process is optimised by finding those conditions which give a maximum amount of *Staphylococcus aureus* 16S ribosomal RNA as detected by probing Northerns with a suitably labelled sequence specific oligonucleotide probe. Typically, a 5' dye labelled primer is used in each PCR primer pair in a PCR reaction which is terminated optimally between 8 and 25 cycles. The PCR products are separated on 6% polyacrylamide gels with detection and quantification using GeneScanner (manufactured by ABI).

Each of these techniques may have advantages or disadvantages depending on the particular application. The skilled artisan would choose the approach that is the most relevant with the particular end use in mind.

Use of the of these technologies when applied to the ORFs of the present invention enables identification of bacterial proteins expressed during infection, inhibitors of which would have utility in anti-bacterial therapy.

The invention relates to novel polypeptides and polynucleotides as described in greater detail below. In particular, the invention relates to polypeptides and polynucleotides of *Staphylococcus aureus*, which is related by amino acid sequence homology to known polypeptide as set forth in Table 1. The invention relates especially to compounds having the nucleotide and amino acid sequence selected from the group consisting of the sequences set out in the Sequence Listing, and to the nucleotide sequences of the DNA in the deposited strain and amino acid sequences encoded thereby.

Deposited materials

A deposit containing a *Staphylococcus aureus* WCUH 29 strain has been deposited with the National Collections of industrial and Marine Bacteria Ltd. (herein "NCIMB"), 23 St. Machar Drive, Aberdeen AB2 1RY, Scotland on Sep. 11, 1995 and assigned NCIMB Deposit No. 40771, and referred to as *Staphylococcus aureus* WCUH29 on deposit. The *Staphylococcus aureus* strain deposit is referred to herein as "the deposited strain" or as "the DNA of the deposited strain".

The deposited strain contains the full length genes comprising the polynucleotides set forth in the Sequence Listing. The sequence of the polynucleotides contained in the deposited strain, as well as the amino acid sequence of the polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

A license may be required to make, use or sell the deposited strain, and compounds derived therefrom, and no such license is hereby granted.

Polypeptides

The polypeptides of the invention include the polypeptides set forth in the Sequence Listing (in particular the mature polypeptide) as well as polypeptides and fragments, particularly those which have the biological activity of a polypeptide of the invention, and also those which have at least 50%, 60% or 70% identity to a polypeptide sequence selected from the group consisting of the sequences set out in the Sequence Listing or the relevant portion preferably at least 80% identity to a polypeptide sequence selected from the group consisting of the sequences set out in the Sequence Listing, and more preferably at least 90% similarity (more preferably at least 90% identity) to a polypeptide sequence selected from the group consisting of the sequences set out in the Sequence Listing, and still more preferably at least 95% similarity (still more preferably at least 95% identity) to a polypeptide sequence selected from the group consisting of the sequences set out in the Sequence Listing, and also include portions of such polypeptides with such portion of the polypeptide generally containing at least 30 amino acids and more preferably at least 50 amino acids.

The invention also includes polypeptides of the formula:

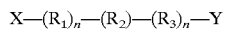

$$X—(R_1)_n—(R_2)—(R_3)_n—Y$$

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly an amino acid sequence selected from the group set forth in the Sequence Listing. In the formula above $R_2$ is oriented so that its amino terminal residue is at the left, bound to $R_1$, and its carboxy terminal residue is at the right, bound to $R_3$. Any stretch of amino acid residues denoted by either R group, where R is greater than 1, may be either a heteropolymer or a homopolymer, preferably a heteropolymer.

A fragment is a variant polypeptide having an amino acid sequence that entirely is the same as part but not all of the amino acid sequence of the aforementioned polypeptides. As with polypeptides, fragments may be "free-standing," or comprised within a larger polypeptide of which they form a part or region, most preferably as a single continuous region, a single larger polypeptide.

Preferred fragments include, for example, truncation polypeptides having a portion of the amino acid sequence of the Sequence Listing, or of variants thereof, such as a continuous series of residues that includes the amino terminus, or a continuous series of residues that includes the carboxyl terminus. Degradation forms of the polypeptides of the invention in a host cell, particularly a *Staphylococcus aureus*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of polypeptides of the invention, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of *Staphylococcus aureus* or the ability to initiate, or maintain cause disease in an individual, particularly a human.

Variants that are fragments of the polypeptides of the invention may be employed for producing the corresponding full-length polypeptide by peptide synthesis; therefore, these variants may be employed as intermediates for producing the full-length polypeptides of the invention.

In addition to the standard single and triple letter representations for amino acids, the term "X" or "Xaa" is also used. "X" and "Xaa" mean that any of the twenty naturally occuring amino acids may appear at such a designated position in the polypeptide sequence.

The initial amino acid encoded by the codon "GTG" is indicated in at least one SEQ ID as valine. However, in one embodiment of the invention, this initial amino acid of a polypeptide of the invention is methionine.

Polynucleotides

Another aspect of the invention relates to isolated polynucleotides that encode the polypeptides of the invention having a deduced amino acid sequence selected from the group consisting of the sequences in the Sequence Listing and polynucleotides closely related thereto and variants thereof.

Using the information provided herein, such as the polynucleotide sequences set out in the Sequence Listing, a polynucleotide of the invention encoding polypeptide may be obtained using standard cloning and screening methods, such as those for cloning and sequencing chromosomal DNA fragments from bacteria using *Staphylococcus aureus* WCUH 29 cells as starting material, followed by obtaining a full length clone. For example, to obtain a polynucleotide sequence of the invention, such as a sequence set forth in the Sequence Listing, typically a library of clones of chromosomal DNA of *Staphylococcus aureus* WCUH 29 in *E. coli* or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Illustrative of the invention, the polynucleotides set out in the Sequence Listing were discovered in a DNA library derived from *Staphylococcus aureus* WCUH 29.

The DNA sequences set out in the Sequence Listing each contain at least one open reading frame encoding a protein having at least about the number of amino acid residues set forth in the Sequence Listing. The start and stop codons of each open reading frame (herein "ORF") DNA are the first three and the last three nuclotides of each polynucleotide set forth in the Sequence Listing.

Certain polynucleotides and polypeptides of the invention are structurally related to known proteins as set forth in Table 1. These proteins exhibit greatest homology to the homologue listed in Table 1 from among the known proteins.

The invention provides a polynucleotide sequence identical over its entire length to each coding sequence in the Sequence Listing. Also provided by the invention is the coding sequence for the mature polypeptide or a fragment thereof, by itself as well as the coding sequence for the mature polypeptide or a fragment in reading fragment with other coding sequence, such as those encoding a leader or secretory sequence, a pre-, or pro- or prepro-protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA tag (Wilson et al., *Cell* 37: 767 (1984). Polynucleotides of the invention also include, but are not limited to, polynucleotides comprising a structural gene and its naturally associated sequences that control gene expression.

The invention also includes polynucleotides of the formula:

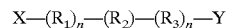

wherein, at the 5' end of the molecule, X is hydrogen, and at the 3' end of the molecule, Y is hydrogen or a metal, $R_1$ and $R_3$ is any nucleic acid residue, n is an integer between 1 and 3000, and $R_2$ is a nucleic acid sequence of the invention, particularly a nucleic acid sequence selected from the group set forth in the Sequence Listing. In the polynucleotide formula above $R_2$ is oriented so that its 5' end residue is at the left, bound to $R_1$, and its 3' end residue is at the right, bound to $R_3$. Any stretch of nucleic acid residues denoted by either R group, where R is greater than 1, may be either a heteropolymer or a homopolymer, preferably a heteropolymer. In a preferred embodiment n is an integer between 1 and 1000.

The term "polynucleotide encoding a polypeptide" as used herein encompasses polynucleotides that include a sequence encoding a polypeptide of the invention, particularly a bacterial polypeptide and more particularly a polypeptide of the *Staphylococcus aureus* having an amino acid sequence set out in the Sequence Listing. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having the deduced amino acid sequence of the Sequence Listing. Variants that are fragments of the polynucleotides of the invention may be used to synthesize full-length polynucleotides of the invention.

Further particularly preferred embodiments are polynucleotides encoding polypeptide variants, that have the amino acid sequence of a polypeptide of the Sequence Lists in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of such polynucleotide.

Further preferred embodiments of the invention are polynucleotides that are at least 50%, 60% or 70% identical over their entire length to a polynucleotide encoding a polypeptide having the amino acid sequence set out in the Sequence Listing, and polynucleotides that are complementary to such polynucleotides. Alternatively, most highly preferred are polynucleotides that comprise a region that is at least 80% identical over its entire length to a polynucleotide encoding a polypeptide of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

A preferred embodiment is an isolated polynucleotide comprising a polynucleotide sequence selected from the group consisting of a polynucleotide having at least a 50% identity to a polynucleotide encoding a polypeptide comprising the amino acid sequence of the Sequence Listing and obtained from a prokaryotic species other than *Staphylococcus aureus*; and a polynucleotide encoding a polypeptide comprising an amino acid sequence which is at least 50% identical to the amino acid sequence of the Sequence Listing and obtained from a prokaryotic species other than *Staphylococcus aureus*.

Preferred embodiments are polynucleotides that encode polypeptides that retain substantially the same biological function or activity as the mature polypeptide encoded by the DNA of the Sequence Listing.

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence set forth in the Sequence Listing under stringent hybridization conditions with a probe having the sequence of said polynucleotide sequence or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding a polypeptide and to isolate cDNA and genomic clones of other genes that have a high sequence simiarity to a polynucleotide set forth in the Sequence Listing. Such probes generally will comprise at least 15 bases. Preferably, such probes will have at least 30 bases and may have at least 50 bases. Particularly preferred probes will have at least 30 bases and will have 50 bases or less.

For example, the coding region of each gene that comprises or is comprised by a polynucleotide set forth in the Sequence Listing may be isolated by screening using a DNA sequence provided in the Sequence Listing to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed, for example, as research reagents and materials for discovery of treatments of and diagnostics for disease, particularly human disease, as further discussed herein relating to polynucleotide assays.

Polynucleotides of the invention that are oligonucleotides derived from the a polynucleotide or polypeptide sequence set forth in the Sequence Listing may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleic acid bases, the term "N" is also used. "N" means that any of the four DNA or RNA bases may appear at such a designated position in the DNA or RNA sequence, except it is preferred that N is not a base that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, host cells, expression

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, enterorococci E. coli, streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmid, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the polynucleotides of the invention for use as diagnostic reagents. Detection of such polynucleotides in a eukaryote, particularly a mammal, and especially a human, will provide a diagnostic method for diagnosis of a disease. Eukaryotes (herein also "individual(s)"), particularly mammals, and especially humans, infected with an organism comprising a gene of the invention may be detected at the nucleic acid level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterizaton of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing amplified DNA to labeled polynucleotide sequences of the invention. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., Science, 230: 1242 (1985). Sequence changes at specific locations also may be revealed by nuclease protection assays, such as RNase and S1 protection or a chemical cleavage method. See, e.g., Cotton et al., Proc. Natl. Acad. Sci., USA, 85: 4397–4401 (1985).

Cells carrying mutations or polymorphisms in the gene of the invention may also be detected at the DNA level by a variety of techniques, to allow for serotyping, for example . For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to a nucleic acid encoding a polypeptide of the invention can be used to identify and analyze mutations. These primers may be used for, among other things, amplifying a DNA of the invention isolated from a sample derived from an individual. The primers may be used to amplify the gene isolated from an infected individual such that the gene may then be subject to various techniques for elucidation of the DNA sequence. In this way, mutations in the DNA sequence may be detected and used to diagnose infection and to serotype and/or classify the infectious agent.

The invention further provides a process for diagnosing, disease, preferably bacterial infections, more preferably infections by Staphylococcus aureus, and most preferably disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric abscess, toxic shock syndrome), skin (e.g., impetigo, folliculitis, cutaneous abscesses, cellulitis, wound infection, bacterial myositis) bone and joint (e.g., septic arthritis, osteomyelitis), comprising determining from a sample derived from an individual a increased level of expression of polynucleotide having the sequence of the Sequence Listing.

Increased or decreased expression of a polynucleotide of the invention can be measured using any on of the methods well known in the art for the quantitation of polynucleotides, such as, for example, amplification, PCR, RT-PCR, RNase protection, Northern blotting and other hybridization methods.

In addition, a diagnostic assay in accordance with the invention for detecting over-expression of a polypeptide of the invention compared to normal control tissue samples may be used to detect the presence of an infection, for example. Assay techniques that can be used to determine levels of a protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an imnunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by adminstering the polypeptides or epitope-bearing fragments, analogues or cells to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein C., *Nature* 256: 495–497 (1975); Kozbor et al., *Immunology Today* 4: 72 (1983); Cole et al., pg. 77–96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology may be utilized to select antibody genes with binding activities towards the polypeptide either from repertoires of PCR amplified v-genes of lymphocytes from humans screened for possessing recognition of a polypeptide of the invention or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones expressing the polypeptides to purify the polypeptides by affinity chromatography.

Thus, among others, antibodies against a polypeptide of the invention may be employed to treat infections, particularly bacterial infections and especially disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric abscess, toxic shock syndrome), skin (e.g., impetigo, folliculitis, cutaneous abscesses, cellulitis, wound infection, bacterial myositis) bone and joint (e.g., septic arthritis, osteomyelitis).

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized"; where the complimentarily determining region(s) of the hybridoma-derived antibody has been transplanted into a human monoclonal antibody, for example as described in Jones, P. et al. (1986), *Nature* 321, 522–525 or Tempest et al.,(1991) *Biotechnology* 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem. 1989: 264,16985), coprecipitation of DNA with calcium phosphate (Benvenisty & Reshef, PNAS, 1986:83, 9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS 1984:81, 5849).

Antagonists and agonists—assays and molecules

Polypeptides of the invention may also be used to assess the binding of small molecule substrates and ligands in, for example, cells, cell-free preparations, chemical libraries, and natural product mixtures. These substrate and ligands may be natural substrates and ligands or may be structural or functional mimetics. See, e.g., Coligan et al., *Current Protocols in Immunology* 1(2): Chapter 5 (1991).

The invention also provides a method of screening compounds to identify those which enhance (agonist) or block (antagonist) the action of a polypeptides or polynucleotides of the invention, particularly those compounds that are bacteriostatic and/or bacteriocidal. The method of screening may involve high-throughput techniques. For example, to screen for agonists or antagonists, a synthetic reaction mix, a cellular compartment, such as a membrane, cell envelope or cell wall, or a preparation of any thereof, comprising a polypeptide of the invention and a labeled substrate or ligand of such polypeptide is incubated in the absence or the presence of a candidate molecule that may be an agonist or antagonist of a polypeptide of the invention. The ability of the candidate molecule to agonize or antagonize a polypeptide of the invention is reflected in decreased binding of the labeled ligand or decreased production of product from such substrate. Molecules that bind gratuitously, i.e., without inducing the effects of a polypeptide of the invention are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to colorimetric labeled substrate converted into product, a reporter gene that is responsive to changes in polynucleotide or polypeptide activity, and binding assays known in the art.

Another example of an assay for antagonists of polypeptides of the invention is a competitive assay that combines any such polypeptide and a potential antagonist with a compound which binds such polypeptide, natural substrates or ligands, or substrate or ligand mimetics, under appropriate conditions for a competitive inhibition assay. A polypeptide of the invention can be labeled, such as by radioactivity or a colorimetric compound, such that the number of such polypeptide molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing activities induced by a polypeptide of the invention, thereby preventing the action of such polypeptide by excluding it from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); OLIGODEOXYNUCLEOTIDES AS ANTISENSE INHIBITORS OF GENE EXPRESSION, CRC Press, Boca Raton, Fla. (1988), for a description of these molecules). Preferred potential antagonists include compounds related to and variants of a polypeptide of the invention.

Each of the DNA sequences provided herein may be used in the discovery and development of antibacterial compounds. The encoded protein, upon expression, can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequels of infection. In particular the molecules of the invention may be used: in the prevention of adhesion of bacteria, in particular gram positive bacteria, to mammalian extracellular matrix proteins on in-dwelling devices or to extracellular matrix proteins in wounds; to block protein-mediated mammalian cell invasion by, for example, initiating phosphorylation of mammalian tyrosine kinases (Rosenshine et al., *Infect. Immun.* 60:2211 (1992); to block bacterial adhesion between mammalian extracellular matrix proteins and bacterial proteins that mediate tissue damage and; to block the normal progression of pathogenesis in infections initiated other than by the implantation of in-dwelling devices or by other surgical techniques.

The antagonists and agonists of the invention may be employed, for instance, to inhibit and treat disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastroinestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric abscess, toxic shock syndrome), skin (e.g., impetigo, folliculitis, cutaneous abscesses, cellulitis, wound infection, bacterial myositis) bone and joint (e.g., septic arthritis, osteomyelitis).

*Helicobacter pylori* (herein *H. pylori*) bacteria infect the stomachs of over one-third of the world's population causing stomach cancer, ulcers, and gastritis (International Agency for Research on Cancer (1994) Schistosomes, Liver Flukes and *Helicobacter Pylori* (International Agency for Research on Cancer, Lyon, France; http://www.uicc.ch/ecp/ecp2904.htm). Moreover, the international Agency for Research on Cancer recently recognized a cause-and-effect relationship between *H. pylori* and gastric adenocarcinoma, classifying the bacterium as a Group I (definite) carcinogen. Preferred antimicrobial compounds of the invention found using screens provided by the invention, particularly broad-spectrum antibiotics, should be useful in the treatment of *H. pylori* infection. Such treatment should decrease the advent of *H. pylori*-induced cancers, such as gastrointestinal carcinoma. Such treatment should also cure gastric ulcers and gastritis.

Vaccines

Another aspect of the invention relates to a method for inducing an immunological response in an individual, particularly a mammal which comprises inoculating the individual with a polypeptide of the invention, or a fragment or variant thereof, adequate to produce antibody and/or T cell immune response to protect said individual from infection, particularly bacterial infection and most particularly *Staphylococcus aureus* infection. Also provided are methods whereby such immunological response slows bacterial replication. Yet another aspect of the invention relates to a method of inducing immunological response in an individual which comprises delivering to such individual a nucleic acid vector to direct expression of a polynucleotide or polypeptide of the invention, or a fragment or a variant thereof, for expressing such polynucleotide or polypeptide, or a fragment or a variant thereof in vivo in order to induce an immunological response, such as, to produce antibody and/or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise.

Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to a polynucleotide of the invention or protein coded therefrom, wherein the composition comprises a recombinant polynucleotide or protein coded therefrom comprising DNA which codes for and expresses an antigen of said polynucleotide or protein coded therefrom. The immunological response may be used therapeutically or prophylactically and may take the form of antibody immunity or cellular immunity such as that arising from CTL or CD4+ T cells.

A polypeptide of the invention or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae,* Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Staphylococcus aureus* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Staphylococcus aureus* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain protein, such as, for example, those set forth in the Sequence Listing, it is to be understood that this covers fragments of the naturally occurring protein and similar proteins with additions, deletions or substitutions which do not substantially affect the immunogenic properties of the recombinant protein.

Compositions, kits and administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administation on by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *Staphylococcus aureus* wound infections.

Many orthopedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 µg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Each reference disclosed herein is incorporated by reference herein in its entirety. Any patent application to which this application claims priority is also incorporated by reference herein in its entirety.

Tables

Certain pertinent data for each of the polypeptides and polynucleotides set forth in the Sequence Listing are summarized in the following Table.

TABLE 1

Provided in this Table is the closest homologue of each polypeptide encoded by each ORF of the invention based on a comparison of the sequences of in the Sequence Listing with sequences available in the public domain (see, the column labeled "Homologue identification"). Preferred polypeptides encoded by the ORFs of the invention, particularly full length proteins either obtained using such ORFs or encoded entirely by such ORFs, are ones that have a biological function of the homologue listed, among other functions. The analysis used to determine each homologue listed in Table 1 was either BlastP, BlastX or MPSearch, each of which is well known. The left-most column of the table shows the relationship between each polynucleotide of the invention and a deduced polypeptide that it encodes. The column labeled "primer pair" shows the left and right primers used to amplify the polynucleotide in the left-most column. These primers may also be used to show in vivo expression or each gene, using one of the mouse models described herein, for example. The right-most column shows the detection of an expression product from the polynucleotide and the infection model in which it was detected.

| Related Polynucleotide and polypeptide SEQ ID NO: | Primer pair SEQ ID NO: (left/right) | Homologue identification | in vivo expression |
|---|---|---|---|
| 1/11 | 21/22 | sp\|P46352\|RIPX_BACSU PROBABLE INTEGRASE/RECOMBINASE RIPX . . . 1.1e-67 | 3 day groin positive 8 day pyelonephritis positive |
| 2/12 | 23/24 | gi\|1934606 (U93874) cystathionine gamma-lyase [. . . 1.4e-53 | 3 day groin positive 8 day pyelonephritis positive |
| 3/13 | 25/26 | gnl\|PID\|d1017321 (D90899) DNA ligase [Synechocystis sp.] 1.1e-115 | 3 day groin positive 8 day pyelonephritis positive |
| 4/14 | 27/28 | gnl\|PID\|e220318 (X95439) ccpA [*Staphylococcus xylosus*] 6.4e-63 | 3 day groin positive 8 day pyelonephritis positive |
| 5/15 | 29/30 | sp\|P35011\|ATPF_GALSU ATP SYNTHASE B CHAIN (SUBUNIT I) >pi. . . | 3 day groin positive 8 day pyelonephritis positive |
| 6/16 | 31/32 | (AF008220) NifS2 [*Bacillus subtilis*] 1.0e-39 | 3 day groin positive 8 day pyelonephritis positive |

TABLE 1-continued

| | | | |
|---|---|---|---|
| 7/17 | 33/34 | >gnl\|PID\|d1019189 (D90914) ClpB [Synechocystis sp.] | 3 day groin positive 8 day pyelonephritis positive |
| 8/18 | 35/36 | gi\|1732203 (U65015) GlcNAc 6-P deacetylase [Vib. . . 3.7e-17 | 3 day groin positive 8 day pyelonephritis positive |
| 9/19 | 37/38 | sp\|P28294\|PYRD_AGRAE DIHYDROOROTATE DEHYDROGENASE (DIHYDR. . . 7.3e-18 | 3 day groin positive 8 day pyelonephritis positive |
| 10/20 | 39/40 | sp\|P44770\|OTC_HAEIN ORNITHINE CARBAMOYLTRANSFERA SE (OTCA. . . 3.7e-99 | 3 day groin positive 8 day pyelonephritis positive |
| 41/47 | 21/22 | sp\|P46352\|RIPX_BACSU PROBABLE INTEGRASE/RECOMBINAS E RIPX. . . 1.1e-67 | 3 day groin positive 8 day pyelonephritis positive |
| 42/48 | 23/24 | gi\|1934606 (u93874) cystathionine gamma-lyase [. . . 1.4e-53 | 3 day groin positive 8 day pyelonephritis positive |
| 43/49 | 27/28 | gnl\|PID\|e220318 (X95439) ccpA [Staphylococcus xylosus] 6.4e-63 | 3 day groin positive 8 day pyelonephritis positive |
| 44/50 | 31/32 | (AF008220) NifS2 [Bacillus subtilis] 1.0e-39 | 3 day groin positive 8 day pyelonephritis positive |
| 45/51 | 35/36 | gi\|1732203 (U65015) GlcNAc 6-P deacetylase [Vib. . . 3.7e-17 | 3 day groin positive 8 day pyelonephritis positive |
| 46/52 | 39/40 | sp\|P44770\|OTC_HAEIN ORNITHINE CARBAMOYLTRANSFERA SE (OTCA. . . 3.7e-99 | 3 day groin positive 8 day pyelonephritis positive |

EXAMPLES

The examples below are carried out using standard techniques, which are well known and routine to those of skill in the art, except where otherwise described in detail. The examples are illustrative, but do not limit the invention.

Example 1

Strain Selection, Library Production and Sequencing

Each polynucleotide having a DNA sequence given in the Sequence Listing was obtained from a library of clones of chromosomal DNA of *Staphylococcus aureus* in *E. coli*. The sequencing data from two or more clones containing overlapping *Staphylococcus aureus* DNAs was used to construct the contiguous DNA sequence in the Sequence Listing. Libraries may be prepared by routine methods, for example: Methods 1 and 2 below.

Total cellular DNA is isolated from *Staphylococcus aureus* WCUH 29 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Example 2

The Determination of Expression During Infection of a Gene from *Staphylococcus aureus*

Necrotic fatty tissue from a 72 hour groin infection or an excised kidney from an 8 day chronic kidney infection of *Staphylococcus aureus* WCUH29 in the mouse is efficiently disrupted and processed in the presence of chaotropic agents and RNAase inhibitor to provide a mixture of animal and bacterial RNA. The optimal conditions for disruption and processing to give stable preparations and high yields of bacterial RNA are followed by the use of hybridisation to a radiolabelled oligonucleotide specific to *Staphylococcus aureus* 16S RNA on Northern blots. The RNAase free, DNAase free, DNA and protein free preparations of RNA obtained are suitable for Reverse Transcription PCR (RT-PCR) using unique primer pairs designed from the sequence of each gene of *Staphylococcus aureus* WCUH29.

a) Isolation of tissue infected with *Staphylococcus aureus* WCUH29 from a mouse animal model of infection (groin): 10 ml. volumes of sterile nutrient broth No.2 Oxoid) are seeded with isolated, individual colonies of *Staphylococcus aureus* WCUH29 from an agar culture plate. The cultures are incubated aerobically (static culture) at 37° C. for 16–20 hours. 4 week old mice (female,18 g–22 g, strain MF1) are each infected by subcutaneous injection of 0.5 ml. of this broth culture of *Staphylococcus aureus* WCUH29 (diluted in broth to approximately $10^8$ cfu/ml.) into the anterior, right lower quadrant (groin area). Mice are monitored regularly during the first 24 hours after infection, then daily until termination of study. Animals with signs of systemic infection, i.e. lethargy, ruffled appearance, isolation from group, should be monitored closely and if signs progress to moribundancy, the animal should be culled immediately.

Visible external signs of lesion development will be seen 24–48 hours after infection. Examination of the abdomen of the animal will show the raised outline of the abscess beneath the skin. The localized lesion should remain in the right lower quadrant, but may occasionally spread to the left lower quadrant, and superiorly to the thorax. On occasions, the abscess may rupture through the overlying skin layers. In such cases the affected animal should be culled immediately and the tissues sampled if possible. Failure to cull the animal may result in the necrotic skin tissue overlying the abscess being sloughed off, exposing the abdominal muscle wall.

Approximately 96 hours after infection, animals are killed using carbon dioxide asphyxiation. To minimise delay between death and tissue processing/storage, mice should be killed individually rather than in groups. The dead animal is placed onto its back and the fur swabbed liberally with 70% alcohol. An initial incision using scissors is made through the skin of the abdominal left lower quadrant, travelling superiorly up to, then across the thorax. The incision is completed by cutting inferiorly to the abdominal lower right quadrant. Care should be taken not to penetrate the abdominal wall. Holding the skin flap with forceps, the skin is gently pulled way from the abdomen. The exposed abscess, which covers the peritoneal wall but generally does not penetrate the muscle sheet completely, is excised, taking care not to puncture the viscera. The abscess/muscle sheet and other infected tissue may require cutting in sections, prior to flash-freezing in liquid nitrogen, thereby allowing easier storage in plastic collecting vials.

b) Isolation of tissue infected with *Staphylococcus aureus* WCUH29 from a murine model of hematogenous pyelonephritis: Overnight cultures of *S. aureus* WCUH29 were started from single colonies in 5 ml of tryptic soy broth (TSB) and grown at 37° C. with shaking. The cultures were then washed twice in sterile phosphate-buffered saline (PBS) and diluted to an $A_{600}$ of 0.3. Male CD-1 mice (18–20 g) were infected with 0.2 ml of this suspension by tail vein inoculation using a 30 g needle attached to a tuberculin syringe. Each mouse receives approximately $4 \times 10^7$ bacteria in this fashion. Mice are monitored daily for signs of illness, and usually within 48 hours show signs of lethargy, ruffled fur, sluggishness; animals which appear moribund are euthanized prior to the end of the experiment.

All animals are euthanized via carbon dioxide overdose seven days post-infection. The animal is placed on its back and swabbed with ethanol, and then with RNAZap, and instruments are swabbed as well. The abdominal cavity is opened and the kidneys aseptically removed, cut into four pieces, and placed in cryovials which are immediately frozen in liquid nitrogen.

c) Isolation of *Staphylococcus aureus* WCUH29 RNA from infected tissue samples: 4–6 infected tissue samples (each approx 0.5–0.7 g) in 2 ml screw-cap tubes are removed from −80° C. storage into a dry ice ethanol bath In a microbiological safety cabinet the samples are disrupted individually whilst the remaining samples are kept cold in the dry ice ethanol bath. To disrupt the bacteria within the tissue sample 1 ml of TRIzol Reagent (Gibco BRL, Life Technologies) is added followed by enough 0.1 mm zirconia/silica beads to almost fill the tube, the lid is replaced taking care not to get any beads into the screw thread so as to ensure a good seal and eliminate aerosol generation. The sample is then homogenised in a Mini-BeadBeater Type BX-4 (Biospec Products). Necrotic fatty tissue isstrain treated for 100 seconds at 5000 rpm in order to achieve bacterial lysis. In vivo grown bacteria require longer treatment than in vitro grown *Staphylococcus aureus* Staphylococcus which are disrupted by a 30 second bead-beat.

After bead-beating the tubes are chilled on ice before opening in a fume-hood as heat generated during disruption may degrade the TRIzol and release cyanide.

200 μl of chloroform is then added and the tubes shaken by hand for 15 seconds to ensure complete mixing. After 2–3 minutes at room temperature the tubes are spun down at 12,000×g, 4° C. for 15 minutes and RNA extraction is then continued according to the method given by the manufacturers of TRIzol Reagent, i.e.:—The aqueous phase, approx 0.6 ml, is transferred to a sterile eppendorf tube and 0.5 ml of isopropanol is added. After 10 minutes at room temperature the samples are spun at 12,000×g, 4° C. for 10 minutes. The supernatant is removed and discarded then the RNA pellet is washed with 1 ml 75% ethanol. A brief vortex is used to mix the sample before centrifuging at 7,500×g, 4° C. for 5 minutes. The ethanol is removed and the RNA pellet dried under vacuum for no more than 5 minutes. Samples are then resuspended by repeated pipetting in 100 μl of DEPC treated water, followed by 5–10 minutes at 55° C. Finally, after at least 1 minute on ice, 200 units of Rnasin (Promega) is added.

RNA preparations are stored at −80° C. for up to one month. For longer term storage the RNA precipitate can be stored at the wash stage of the protocol in 75% ethanol for at least one year at −20° C.

Quality of the RNA isolated is assessed by running samples on 1% agarose gels. 1×TBE gels strained with ethidium bromide are used to visualise total RNA yields. To demonstrate the isolation of bacterial RNA from the infected tissue 1×MOPS, 2.2M formaldehyde gels are run and vacuum blotted to Hybond-N (Amersham). The blot is then hybridised with a $^{32}$P labelled oligonucletide probe specific to 16s rRNA of *Staphylococcus aureus* (K. Greisen, M. Loeffelholz, A. Purohit and D. Leong. J.Clin. (1994) Microbiol. 32 335–351). An oligonucleotide of the sequence: 5'-gctcctaaaaggttactccaccggc-3'[SEQ ID NO:7] is used as a probe. The size of the hybridising band is compared to that of control RNA isolated from in vitro grown *Staphylococcus aureus* WCUH29 in the Northern blot. Correct sized bacterial 16s rRNA bands can be detected in total RNA samples which show extensive degradation of the mammalian RNA when visualised on TBE gels.

d) The removal of DNA from *Staphylococcus aureus* WCUH29-derived RNA: DNA was removed from 73 μl samples of RNA by a 15 minute treatment on ice with 3 units of DNAaseI, amplification grade (Gibco BRL, Life Technologies) in the buffer supplied with the addition of 200 units of Rnasin (Promega) in a final volume of 90 μl.

The DNAase was inactivated and removed by treatment with TRIzol LS Reagent (Gibco BRL, Life Technologies) according to the manufacturers protocol. DNAase treated RNA was resuspended in 73 μl of DEPC treated water with the addition of Rnasin as described in Method 1.

e) The preparation of cDNA from RNA samples derived from infected tissue: 10 μl samples of DNAase treated RNA are reverse transcribed using a SuperScript Preamplification System for First Strand cDNA Synthesis kit (Gibco BRL, Life Technologies) according to the manufacturers instructions. 1 ng of random hexamers is used to prime each reaction. Controls without the addition of SuperScriptII reverse transcriptase are also run. Both +/−RT samples are treated with RNaseH before proceeding to the PCR reaction.

f) The use of PCR to determine the presence of a bacterial cDNA species: PCR reactions are set up on ice in 0.2 ml tubes by adding the following components: 45 μl PCR SUPERMIX (Gibco BRL, Life Technologies); 1 μl 50 mM MgCl₂, to adjust final concentration to 2.5 mM; 1 μl PCR primers (optimally 18–25 basepairs in length and designed to possess similar annealing temperatures), each primer at 10 mM initial concentration; and 2 μl cDNA.

PCR reactions are run on a Perkin Elmner GeneAmp PCR System 9600 as follows: 5 minutes at 95° C., then 50 cycles of 30 seconds each at 94° C., 42° C. and 72° C. followed by 3 minutes at 72° C. and then a hold temperature of 4° C. (the number of cycles is optimally 30–50 to determine the appearance or lack of a PCR product and optimally 8–30 cycles if an estimation of the starting quantity of cDNA from the RT reaction is to be made); 10 μl aliquots are then run out on 1% 1×TBE gels strained with ethidium bromide with PCR product, if present, sizes estimated by comparison to a 100 bp DNA Ladder (Gibco BRL, Life Technologies). Alternatively if the PCR products are conveniently labelled by the use of a labelled PCR primer (e.g. labelled at the 5'end with a dye) a suitable aliquot of the PCR product is run out on a polyacrylamide sequencing gel and its presence and quantity detected using a suitable gel scanning system (e.g. ABI Prism™ 377 Sequencer using GeneScan™ software as supplied by Perkin Elmer).

RT/PCR controls may include +/−reverse transcriptase reactions, 16s rRNA primers or DNA specific primer pairs designed to produce PCR products from non-transcribed *Staphylococcus aureus* WCUH29 genomic sequences.

To test the efficiency of the primer pairs they are used in DNA PCR with *Staphylococcus aureus* WCUH29 total DNA. PCR reactions are set up and run as described above using approx. 1 microgram of DNA in place of the cDNA and 35 cycles of PCR.

Primer pairs which fail to give the predicted sized product in either DNA PCR or RT/PCR are PCR failures and as such are uninformative. Of those which give the correct size product with DNA PCR two classes are distinguished in RT/PCR: (1) genes which are not transcribed in vivo reproducibly fail to give a product in RT/PCR; and (2) genes which are transcribed in vivo reproducibly give the correct size product in RT/PCR and show a stronger signal in the +RT samples than the signal (if at all present) in −RT controls.

Using the method described in this example and primer pairs set forth in the Sequence Listing (see Table 1 for further details), each of the the polynucleotides in the Sequence Listing were demonstrated to be in vivo expressed.

The appended Sequence Listings includes SEQ ID NOS: 1 to 52.

What is claimed is:

1. An isolated polynucleotide segment comprising a nucleic acid sequence, wherein the nucleic acid sequence comprises SEQ ID NO:1, and is not genomic DNA.

2. A vector comprising the isolated polynucleotide segment of claim 1.

3. An isolated host cell comprising the vector of claim 2.

4. A process for producing an amino acid sequence comprising culturing the host cell of claim 3 under conditions sufficient for the production of the amino acid sequence, wherein the amino acid sequence comprises SEQ ID NO:11.

5. An isolated polynucleotide segment comprising a polynucleotide sequence which encodes an amino acid sequence comprising SEQ ID NO:11, wherein the polynucleotide sequence is not genomic DNA.

6. A vector comprising the isolated polynucleotide segment of claim 5.

7. An isolated host cell comprising the vector of claim 6.

8. A process for producing an amino acid sequence comprising culturing the host cell of claim 7 under conditions sufficient for the production of the amino acid sequence, wherein the amino acid sequence comprises SEQ ID NO:11.

9. An isolated polynucleotide segment comprising a polynucleotide sequence which encodes an amino acid sequence consisting of SEQ ID NO:11, wherein the polynucleotide sequence is not genomic DNA.

10. A vector comprising the isolated polynucleotide segment of claim 9.

11. An isolated host cell comprising the vector of claim 10.

12. A process for producing an amino acid sequence comprising culturing the host cell of claim 11 under conditions sufficient for the production of the amino acid sequence, wherein the amino acid sequence consists of SEQ ID NO:11.

* * * * *